United States Patent
Galili et al.

(12) 
(10) Patent No.: US 6,677,506 B1
(45) Date of Patent: Jan. 13, 2004

(54) DNA CODING FOR A $MG^{2+}/H^+$ OR $ZN^{2+}/H^+$ EXCHANGER AND TRANSGENIC PLANTS EXPRESSING SAME

(75) Inventors: Gad Galili, Rehovot (IL); Orit Shaul, Petach Tikva (IL); Dirk Inze, Moorzel-Aalst (BE); Marc Van Montagu, Brussels (BE); Donald W. Hilgemann, Dallas, TX (US)

(73) Assignees: Yeda Research and Development Co. Ltd., Rehovot (IL); The University of Texas System, Austin, TX (US)

( * ) Notice: Subject to any disclaimer, the term of this patent is extended or adjusted under 35 U.S.C. 154(b) by 0 days.

(21) Appl. No.: 09/701,068

(22) PCT Filed: May 25, 1999

(86) PCT No.: PCT/IL99/00277

§ 371 (c)(1), (2), (4) Date: Nov. 24, 2000

(87) PCT Pub. No.: WO99/61616

PCT Pub. Date: Dec. 2, 1999

(30) Foreign Application Priority Data

May 26, 1998 (IL) .................................................. 124653

(51) Int. Cl.[7] ............................ A01H 5/00; C12N 15/82

(52) U.S. Cl. ........................................ 800/298; 435/419

(58) Field of Search ............................... 435/320.1, 419, 435/468; 800/278, 298

(56) References Cited

PUBLICATIONS

Ingram, J. et al. The Molecular Basis of Dehydration Tolerance in Plants. 1996. Annu. Rev. Plant Physiol. Plant Mol. Biol., vol. 47, pp. 377–403.*

* cited by examiner

*Primary Examiner*—Phuong T Bui
*Assistant Examiner*—Cynthia Collins
(74) *Attorney, Agent, or Firm*—G. E. Ehrlich Ltd.

(57) ABSTRACT

An isolated DNA molecule is provided coding for a polypeptide of the 11–12 transmembrane domain transporter family having a $Mg^{2+}/H^+$ or $Zn^{2+}/H^+$ exchange activity, herein designated MHX. The genomic MHX DNA was isolated from *Arabidopsis thaliana* cv. C-24. Transgenic plants transformed with said DNA and expressing MHX are shown to have a lower content of sodium as compared with corresponding wild-type plants or a higher dry matter weight upon growth in calcium-rich media as compared with corresponding wild-type plants. These transgenic plants are tolerant to stress conditions, particularly high salinity and calcium-rich media, e.g. saline and calcareous soils.

4 Claims, 10 Drawing Sheets

```
Met  ala  Ser  Ile  Leu  Asn  Gln  Thr  Gln  Glu  Leu  Gln  Glu  Ser  Ser
               5                        10                       15
Lys  Val  Leu  Gly  His  Leu  Arg  Cys  Glu  Asn  Phe  Phe  Leu  Phe  Pro
               20                       25                       30
Gly  Glu  Asn  Thr  Leu  Ser  Asp  Gly  Leu  Arg  Gly  Val  Leu  Tyr  Phe
               35                       40                       45
Leu  Gly  Leu  Ala  Tyr  Cys  Phe  Ile  Gly  Leu  Ser  Ala  Ile  Thr  Ala
               50                       55                       60
Arg  Phe  Phe  Lys  Ser  Met  Glu  Asn  Val  Val  Lys  His  Ser  Arg  Lys
               65                       70                       75
Val  Val  Thr  Ile  Asp  Pro  Ile  Thr  Lys  Ala  Glu  Val  Ile  Thr  Tyr
               80                       85                       90
Lys  Lys  Val  Trp  Asn  Phe  Thr  Ile  Ala  Asp  Ile  Ser  Leu  Leu  Ala
               95                      100                      105
Phe  Gly  Thr  Ser  Phe  Pro  Gln  Ile  Ser  Leu  Ala  Thr  Ile  Asp  Ala
              110                      115                      120
Ile  Arg  Asn  Met  Gly  Glu  Arg  Tyr  Ala  Gly  Gly  Leu  Gly  Pro  Gly
              125                      130                      135
Thr  Leu  Val  Gly  Ser  Ala  Ala  Phe  Asp  Leu  Phe  Pro  Ile  His  Ala
              140                      145                      150
Val  Cys  Val  Val  Val  Pro  Lys  Ala  Gly  Glu  Leu  Lys  Lys  Ile  Ser
              155                      160                      165
Asp  Leu  Gly  Val  Trp  Leu  Val  Glu  Leu  Val  Trp  Ser  Phe  Trp  Ala
              170                      175                      180
Tyr  Ile  Trp  Leu  Tyr  Ile  Ile  Leu  Glu  Val  Trp  Ser  Pro  Asn  Val
              185                      190                      195
Ile  Thr  Leu  Val  Glu  Ala  Leu  Leu  Thr  Val  Leu  Gln  Tyr  Gly  Leu
              200                      205                      210
Leu  Leu  Val  His  Ala  Tyr  Ala  Gln  Asp  Lys  Arg  Trp  Pro  Tyr  Leu
              215                      220                      225
Ser  Leu  Pro  Met  Ser  Arg  Gly  Asp  Arg  Pro  Glu  Glu  Trp  Val  Pro
              230                      235                      240
Glu  Glu  Ile  Asp  Thr  Ser  Lys  Asp  Asp  Asn  Asp  Asn  Asp  Val  His
              245                      250                      255
Asp  Val  Tyr  Ser  Asp  Ala  Ala  Gln  Asp  Ala  Val  Glu  Ser  Gly  Ser
              260                      265                      270
Arg  Asn  Ile  Val  Asp  Ile  Phe  Ser  Ile  His  Ser  Ala  Asn  Asn  Asp
              275                      280                      285
Thr  Gly  Ile  Thr  Tyr  His  Thr  Val  Ala  Asp  Thr  Pro  Pro  Asp  Ser
              290                      295                      300
Ala  Thr  Lys  Lys  Gly  Lys  Ala  Lys  Asn  Ser  Thr  Val  Phe  Asp  Ile
              305                      310                      315
Trp  Lys  His  Gln  Phe  Val  Asp  Ala  Ile  Thr  Leu  Glu  Thr  Ser  Glu
              320                      325                      330
Ser  Lys  Lys  Val  Asp  Ser  Ile  Tyr  Leu  Arg  Ile  Ala  Lys  Ser  Phe
              335                      340                      345
```

```
Trp His Leu Leu Leu Ala Pro Trp Lys Leu Leu Phe Ala Phe Val
            350             355             360
Pro Pro Cys Asn Ile Ala His Gly Trp Ile Ala Phe Ile Cys Ser
            365             370             375
Leu Leu Phe Ile Ser Gly Val Ala Phe Val Val Thr Arg Phe Thr
            380             385             390
Asp Leu Ile Ser Cys Val Thr Gly Ile Asn Pro Tyr Val Ile Ala
            395             400             405
Phe Thr Ala Leu Ala Ser Gly Thr Ser Trp Pro Asp Leu Val Ala
            410             415             420
Ser Lys Ile Ala Ala Glu Arg Gln Leu Thr Ala Asp Ser Ala Ile
            425             430             435
Ala Asn Ile Thr Cys Ser Asn Ser Val Asn Ile Tyr Val Gly Ile
            440             445             450
Gly Val Pro Trp Leu Ile Asn Thr Val Tyr Asn Tyr Phe Ala Tyr
            455             460             465
Arg Glu Pro Leu Tyr Ile Glu Asn Ala Lys Gly Leu Ser Phe Ser
            470             475             480
Leu Leu Ile Phe Phe Ala Thr Ser Val Gly Cys Ile Val Val Leu
            485             490             495
Val Leu Arg Arg Leu Ile Ile Gly Ala Glu Leu Gly Gly Pro Arg
            500             505             510
Leu Trp Ala Trp Leu Thr Ser Ala Tyr Phe Met Met Leu Trp Val
            515             520             525
Val Phe Val Val Leu Ser Ser Leu Lys Val Ser Gly Val Ile
            530             535             539
```

Fig. 1b

```
TCGATTTCCG TTTGTCGGAA AATCTCTCCC GTGATCGGCGT ATTGTGAAT    50
GCCGCTCACC GAGATATTCT CCGATTCTTT TCCCCAGTGAG GACAAGTGT   100
TCAGTTGACT TATTAGGAGG TGGGGTTTGA ATAAGTTACAA TGGCCTCAA   150
TTCTTAATCA AACCCAGGAG TTGCAAGAAT CTTCTAAGGTT CTTGGGCAT   200
TTAAGATGTG AAAACTTCTT TCTATTCCCC GGAGAAAACAC TTTGTCAGA   250
TGGTTTGAGG GGTGTGTTAT ATTTTCTCGG TCTTGCCTACT GCTTTATTG   300
GGTTGTCAGC CATCACTGCA CGGTTCTTCA AGTCTATGGAG AATGTCGTG   350
AAACATTCCC GTAAAGTGGT TACAATTGAT CCCATTACTAA AGCTGAAGT   400
CATCACATAC AAGAAAGTTT GGAACTTTAC TATTGCAGACA TCAGTTTGT   450
TGGCGTTTGG AACTAGCTTC CCTCAGATTT CTTTGGCTACC ATCGATGCA   500
ATACGGAATA TGGGGGAGCG GTATGCTGGA GGTCTTGGTCC TGAACACT    550
TGTTGGCTCA GCTGCATTTG ATCTTTTCCC CATCCACGCTG TTTGTGTCG   600
TTGTGCCAAA AGCTGGAGAA CTGAAAAAGA TATCCGACTTA GGTGTTTGG   650
CTAGTTGAGC TCGTATGGTC TTTTTGGGCT TACATCTGGCT ATACATAAT   700
CCTCGAGGTG TGGTCACCAA ACGTAATTAC ACTTGTGGAGG CATTATTGA   750
CAGTACTGCA ATACGGATTG CTTCTAGTTC ATGCGTACGCC CAAGACAAG   800
CGATGGCCTT ACTTGTCTTT ACCAATGTCA AGAGGTGATAG GCCAGAGGA   850
GTGGGTTCCA GAGGAGATTG ATACATCCAA AGATGACAATG ACAATGATG   900
TTCATGATGT GTATTCGGAT GCTGCTCAAG ATGCTGTTGAA TCGGGAAGC   950
AGAAACATTG TTGATATCTT CTCTATTCAT TCAGCTAACAA TGATACAGG  1000
GATCACTTAT CATACTGTGG CAGATACTCC ACCCGATTCTG CGACTAAGA  1050
AGGGTAAGGC GAAGAATTCT ACTGTTTTTG ACATTTGGAAA CATCAATTC  1100
GTGGATGCAA TAACGTTGGA AACATCAGAA TCAAAGAAAGT GGATAGCAT  1150
TTATCTTCGA ATCGCGAAAT CTTTCTGGCA TTTACTCCTCG CCCCTTGGA  1200
AACTGCTTTT TGCATTTGTG CCCCCCTGCA ACATTGCTCAC GGTTGGATC  1250
GCTTTCATCT GCTCTCTCCT CTTCATCAGT GGAGTAGCCTT TGTTGTCAC  1300
AAGATTTACT GACCTTATAA GCTGTGTCAC TGGAATAAACC CATATGTGA  1350
TAGCATTCAC AGCACTCGCA AGTGGAACTT CATGGCCAGAC TTAGTAGCA  1400
AGTAAAATCG CTGCAGAGCG ACAACTAACC GCAGATTCAGC TATTGCAAA  1450
CATCACCTGC AGTAACTCGG TGAACATCTA TGTGGGGATTG GAGTTCCGT  1500
GGCTGATAAA CACAGTCTAC AACTACTTTG CATACAGAGAG CCTTTATAC  1550
ATAGAAAACG CTAAAGGATT AAGCTTTTCG CTTCTGATATT CTTTGCGAC  1600
ATCAGTGGGA TGTATCGTGG TGCTTGTGTT GAGAAGGTTGA TTATAGGAG  1650
CTGAGCTTGG AGGTCCAAGG CTATGGGCTT GGCTTACTTCT GCCTATTTC  1700
ATGATGCTTT GGGTCGTCTT CGTTGTTCTT TCTTCTTTGAA AGTTTCAGG  1750
CGTCATATAG AAGAAGCAAC AAAAGGAAAA ACCCCATGAGT AGAAGAAAA  1800
AGTCTTAGCT TACTTGCACA TGTCTCAGTT TTTGTTTTTCT TACTTGTTA  1850
AGGGGGTTTT ATATAATTAT CAAAGTTCAA AGGCAGTTGGC TAAATATGT  1900
GTTGCAAATA TAAATCATAT TGACTATGAT TTTGGAGGCTT AAAAAAAAA  1950
```

Fig. 2

```
CCGGTACGTC CGCATTGATC AATTTCGTCG CGTGGCTCAC TCTGTTTCAT    50
CTGTTCTTTT CTTATTTTTT AGCTATTTTT GTTGAGATTT GTTCGTTGAA   100
AATTATGGTT TTGTGAAAAG AACCCAACTT GTTTACTGA ACCCATGATG    150
AAAGTTATAA TCTTTTGATC TGGTTACCTC TGGATTTTGA TTACGCATAC   200
AGTGGAACAT GCAATTGTTA TTAGCATTGG TTATAGATTG GATTTCGGTT   250
ACATGCCATT GGATCCGTTG CAATGTTTAG TTTGTGTTAC AGATTCTCTG   300
GAAAGAAATC TTTTTGCATG TTCCGTTTGT TTCGCATCCT CTTGATACTG   350
TTCGATCGAT CAGGCTACAG GTTTCATCAG TTTCTTCTAA AAGTTGTAAG   400
CTTCTTTTTG GTGTGCCAGA TTCTTTTCCC CAGTGAGGAC AAGTGTTCAG   450
TTGACTTATT AGGAGGTGGG GTTGAATAA GTTACAATGG CCTCAATTCT    500
TAATCAAACC CAGGAGTTGC AAGAATCTTC TAAGGTTCTT GGGCATTTAA   550
GATGTGAAAA CTTCTTTCTA TTCCCCGGAG AAAACACTTT GTCAGATGGT   600
TTGAGGGGTG TGTTATATTT TCTCGGTCTT GCCTACTGCT TTATTGGGTT   650
GTCAGCCATC ACTGCACGGT TCTTCAAGTC TATGGAGAAT GTCGTGAAAC   700
ATTCCCGTAA AGTGGTTACA ATTGATCCCA TTACTAAAGC TGAAGTCATC   750
ACATACAAGA AAGTTTGGAA CTTTACTATT GCAGACATCA GTTTGTTGGC   800
GTTTGGAACT AGCTTCCCTC AGATTTCTTT GGCTACCATC GATGCAATAC   850
GGAATATGGG GGAGCGGTAT GCTGGAGGTC TGGTGGTTGT TCCTTTCTTC   900
CTTCCAAAAC TCTAGTTTTT ACTTTAAGT TCATGAATTC TTATATCATG    950
TTTTGTCATA TAGGTCTTGG TCCTGGAACA CTTGTTGGCT CAGCTGCATT  1000
TGATCTTTTC CCCATCCACG CTGTTTGTGT CGTTGTGCCA AAAGCTGGAG  1050
AACTGAAAAA GATATCCGAC TTAGGTGTTT GGCTAGTTGA GCTCGTATGG  1100
TCTTTTTGGG CTTACATCTG GCTATACATA ATCCTCGAGG TAACTGTGAA  1150
AAGCGGTTTA AACAGATTCT GTTGAGTCTA TACTCTATAC TGATAAGGTC  1200
TAAAAATCTG TTTCTTTTCA CGTCTCACAG GTGTGGTCAC CAAACGTAAT  1250
TACACTTGTG GAGGCATTAT TGACAGTACT GCAATACGGA TTGCTTCTAG  1300
TTCATGCGTA CGCCCAAGAC AAGCGATGGC CTTACTTGTC TTTACCAATG  1350
TGGGTTTCTT TTCCAGACAA TAATATTAGT TCCTTCAAAA TGGATTTCTA  1400
CTAAAGATTG TATCTTTGTG TTTGTATTTG ATACTTGCAG GTCAAGAGGT  1450
GATAGGCCAG AGGAGTGGGT TCCAGAGGAG ATTGATACAT CCAAAGATGA  1500
CAATGACAAT GATGTTCATG ATGTGTATTC GGATGCTGCT CAAGATGCTG  1550
TTGAATCGGG AAGCAGAAAC ATTGTTGATA TCTTCTCTAT TCATTCAGCT  1600
AACAATGATA CAGGTACTAA GTATGATTAG GCTGTCTATT CTATTGATAT  1650
AAGATCAGTT TTAGCGTATT TGCTTATTTC CAAATCTATG TGATTCCCAT  1700
ATTTATCTCT GGTAGTATAT TGTTATAAAT CAAACTTTCC CTGTAACAAA  1750
CACTTTTGCA GGGATCACTT ATCATACTGT GGCAGATACT CCACCCGATT  1800
CTGCGACTAA GAAGGGTAAG GCGAAGAATT CTACTGTTTT TGACATTTGG  1850
AAACATCAAT TCGTGGATGC AATAACGGTA AAAATCTTCA ACTTACCAAG  1900
TGTTTTCTAG ATTCTTCTAT ATCCTATTTT GGGCTTTTGA TCATTATCAA  1950
CACATCTTTC TTAACTTGTT TCTCTTCCTA TTCGTAATCA AACAGTTGGA  2000
AACATCAGAA TCAAAGAAAG TGGATAGCAT TTATCTTCGA ATCGCGAAAT  2050
CTTTCTGGCA TTTACTCCTC GCCCCTTGGA AACTGCTTTT TGCATTTGTG  2100
CCCCCCTGCA ACATTGCTCA CGGTTGGATC GCTTTCATCT GCTCTCTCCT  2150
CTTCATCAGT GGAGTAGCCT TTGTTGTCAC AAGATTACT GACCTTATAA   2200
GCTGTGTCAC TGGTACACAC CCTCACCGCT TTCAAAAACT GAAGTTATAA  2250
GATTAAACAT TTGAGCTCTA AAACATTAGA AACTCTTTTC ATCTTGCAGG  2300
AATAAACCCA TATGTGATAG CATTCACAGC ACTCGCAAGT GGAACTTCAT  2350
```

Fig. 3a

```
GGCCAGACTT AGTAGCAAGT AAAATCGCTG CAGAGCGACA ACTAACCGCA   2400
GATTCAGCTA TTGCAAACAT CACCTGCAGG TAAAAATCTC AAAACCCTTT   2450
ACAAACATTG AAGATCTTTT CATGATCTTT TTGGTGATAA ATTATGCAGT   2500
AACTCGGTGA ACATCTATGT GGGGATTGGA GTTCCGTGGC TGATAAACAC   2550
AGTCTACAAC TACTTTGCAT ACAGAGAGCC TTTATACATA GAAAACGCTA   2600
AAGGATTAAG CTTTTCGCTT CTGATATTCT TTGCGACATC AGTGGGATGT   2650
ATCGTGGTGC TTGTGTTGAG AAGGTTGATT ATAGGAGCTG AGCTTGGAGG   2700
TCCAAGGCTA TGGGCTTGGC TTACTTCTGC CTATTTCATG ATGCTTTGGG   2750
TCGTCTTCGT TGTTCTTTCT TCTTTGAAAG TTTCAGGCGT CATATAGAAG   2800
AAG                                                     2803
```

Fig. 3b

```
  1                                        MASILNQTQELQESS  15  SEQ ID NO:2
                                           ---------------
                     I
 16 KVLGHLRCENFFLFPGENTLSDGLRGVLYFLGLAYCFIGLSAITARFFKS      65
    ----------------------                          ------
                                     II
 66 MENVVKHSRKVVTIDPITKAEVITYKKVWNFTIADISLLAFGTSFPQISL     115
    |||||||||||||||||||||||||||||||||||||||||||||||||
  1 MENVVKHSRKVVTIDPITKAEVITYKKVWNFTIADISLLAFGTSFPQISL      50  SEQ ID NO:5
                   .         III.           .         .
116 ATIDAIRNMGERYAGGLGPGTLVGSAAFDLFPIHAVCVVVPKAGELKKIS     165
    |||||||||||||||||||||||||||||||||||||||||||||||||
 51 ATIDAIRNMGERYAGGLGPGTLVGSAAFDLFPIHAVCVVVPKAGELKKIS     100
          . IV          .             .       .V       .
166 DLGVWLVELVWSFWAYIWLYIILEVWSPNVITLVEALLTVLQYGLLLVHA     215
    |||||||||||||||||||||||||||||||||||||||||||||||||
101 DLGVWLVELVWSFWAYIWLYIILEVWSPNVITLVEALLTVLQYGLLLVHA     150

216 YAQDKRWPYLSLPMSRGDRPEEWVPEEIDTSKDDNDNDVHDVYSDAAQDA     265
    |||||||||||||||||||||||||||||||||||||||||||||||||
151 YAQDKRWPYLSLPMSRGDRPEEWVPEEIDTSKDDNDNDVHDVYSDAAQDA     200

266 VESGSRNIVDIFSIHSANNDTGITYHTVADTPPDSATKKGKAKNSTVFDI     315
    |||||||||||||||||||||||||||||||||||||||||||||||||
201 VESGSRNIVDIFSIHSANNDTGITYHTVADTPPDSATKKGKAKNSTVFDI     250
                                                VI    .
316 WKHQFVDAITLETSESKKVDSIYLRIAKSFWHLLLAPWKLLFAFVPPCNI     365
    ||||||||||..    |||||||||||||||||||||||||||||||||
251 WKHQFVDAITVKIFNLPKVDSIYLRIAKSFWHLLLAPWKLLFAFVPPCNI     300
              .VII       .         .      VIII    .
366 AHGWIAFICSLLFISGVAFVVTRFTDLISCVTGINPYVIAFTALASGTSW     415
    |||||||||||||||||||||||||||||||||||||||||||||||||
301 AHGWIAFICSLLFISGVAFVVTRFTDLISCVTGINPYVIAFTALASGTSW     350
                                             IX.
416 PDLVASKIAAERQLTADSAIANITCSNSVNIYVGIGVPWLINTVYNYFAY     465
    |||||||||||||||||||||||||||||||||||||||||||||||||
351 PDLVASKIAAERQLTADSAIANITCSNSVNIYVGIGVPWLINTVYNYFAY     400
                  . X .
466 REPLYIENAKGLSFSLLIFFATSVGCIVVLVRRLIIGAELGGPRLWAWL      515
    |||||||||||||||||||||||||||||||||||||||||||||||||
401 REPLYIENAKGLSFSLLIFFATSVGCIVVLVRRLIIGAELGGPRLWAWL      450
         XI    .
516 TSAYFMMLWVVFVVLSSLKVSGVI                              539
    ||||||||||||||||||||||||
451 TSAYFMMLWVVFVVLSSLKVSGVI                              474
```

Fig. 4

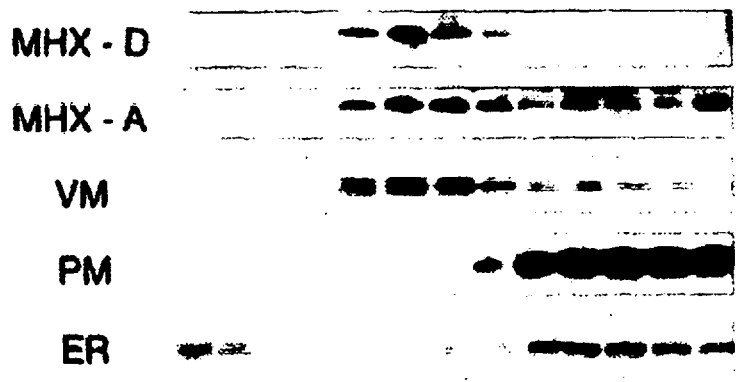
Fig. 5
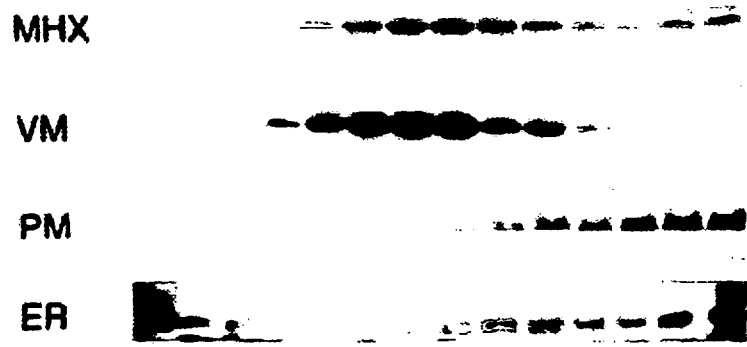
Fig. 6
Fig. 7
Fig. 8

DNA CODING FOR A MG$^{2+}$/H$^+$ OR ZN$^{2+}$/H$^+$ EXCHANGER AND TRANSGENIC PLANTS EXPRESSING SAME

FIELD AND BACKGROUND OF THE INVENTION

The present invention relates in general to DNA molecules encoding a new polypeptide of the 11–12 transmembrane domain transporter family having a Mg$^{2+}$- or Zn$^{2+}$-proton exchange activity, expression vectors comprising them, plant cells transformed thereby and transgenic plants expressing same.

In all living organisms, cellular functions require a fine homeostasis of various ions and nutrients, including Mg$^{2+}$ and Zn$^2$+. Mg$^{2+}$ is required for the function of manv enzymes (e.g., phosphatases, ATPases. RNA polymerases). Zn$^{2+}$ plays both a functional (catalytic) and structural role in several enzyme reactions, and is involved in the regulation of gene expression by zinc-finger proteins. Both Mg$^{2+}$ and Zn$^{2+}$ are essential for the structural integrity of ribosomes. In plants, Mg$^{2+}$ is also an essential component of chlorophyll, and regulates the activity of key chloroplastic enzymes.

Multicellular organisms have to balance not only their Mg$^{2+}$ and Zn$^{2+}$ intake and intracellular compartmentalization. but also the distribution of these ions to various organs. The movement of ions through membrane barriers is mediated by specialized proteins—channels, transporters or ATPases. Thus far, genes encoding Mg$^{2+}$ transporters have been cloned only from bacteria and yeast. The bacterial MgtA and MgtB Mg$^{2+}$ transport proteins are P-type ATPases (Hmiel et al., 1989). Mg$^{2+}$ is also transported by the bacterial CorA and mgtE proteins (Smith et al., 1993; Smith et al., 1995), but the molecular mechanism of Mg$^{2+}$ mobilization by these proteins is not known. Among the Zn$^{2+}$ transport proteins whose genes have been cloned, the bacterial ZntA (Rensing et al., 1997) is a P-type ATPase. Zn$^{2+}$ is also transported by the yeast ZRT 1,2 (Zhao and Eide, 1996a; Zhao and Eide, 1996b), transporters, but the molecular mechanism of Zn$^{2+}$ transport by these proteins is also unknown. A mammalian protein designated DCT1 (Gunshin el al., 1997), which belongs to the Nramp family of macrophage proteins, was suggested to be a symporter of protons with various divalent metal cations, including Fe$^{2+}$ and Zn$^2$+, but it was not able to symport Mg$^{2+}$ ions.

Little is known about transport proteins that control. Mg$^{2+}$ and Zn$^{2+}$ homeostasis in plants. Ions absorbed into the cytosol of root cells diffuse towards the vascular cylinder through plasmodesmata and reach the xylem parenchyma cell layer, which border the xylem vessels. The xylem parenchyrna cells were suggested to play a key role in ion secretion into the xylem (xylem loading), and in the release of ions from the xylem (unloading). These processes require transport through the plasma membrane of the xylem parenchyma cells, but the proteins mediating xylem loading and unloading of Mg$^{2+}$ and Zn$^{2+}$ are not known. Unloaded Mg$^{2+}$ and Zn$^{2+}$ subsequently enter the surrounding cells through unknown transport proteins. The molecular mechanisms of phloem loading and unloading with Mg$^{2+}$ and Zn$^{2+}$ have also not been elucidated. Intracellularly, the vacuole is considered the main organelle mediating Mg$^{2+}$ homeostasis in the cytosol and the chloroplast. Vacuolar Mg$^{2+}$ is also important for the cation-anion balance and turgor regulation of cells. The activity of a Mg$^{2+}$/H$^+$ antiporter was identified in lutoid (vacuolar) vesicles of *Hevea brasiliensis* (Amalou et al., 1992; Amalou et al., 1994) and in vacuolar membranes from roots of *Zea mays L.* (Pfeiffer and Hager, 1993), but cloning of the corresponding genes has not been reported. The *Hevea brasiliensis* transporter was indicated to be electroneutral, and to be capable of transporting also Zn$^{2+}$ cations. In Zn$^{2+}$ tolerant species, tolerance is achieved mainly through sequestering Zn$^{2+}$ in the vacuoles, but the transport mechanism is not known.

The progressive salinization of irrigated land threatens the future of agriculture in the most productive areas of our planet. Increasingly, intensive irrigation practices are resulting in secondary salinization of agricultural soils. Even water of good quality may contain 100–1000 g salt/m$^3$. With an annual application of 10,000 m$^3$/ha, between 1 and 10 t of salt are added to the soil. As a result of transpiration and evaporation of water, soluble salts further accumulate in the soil. Since crop productivity of irrigated land in many areas is much higher than of non-irrigated land, the coincidence of irrigation and salinization threatens current agricultural productivity. It has been estimated that 10×10$^6$ ha per annum of irrigated land are abandoned due to salinization and alkalization. For example, large areas of the Indian subcontinent have been rendered unproductive by salt accumulation and poor water management; in Pakistan, about 10 million of 15 million hectares of canal-irrigated land are becoming saline. Worldwide, about 33% of the irrigated land is affected by salinity, and presumably more land is going out of irrigation due to salinity than there is new land coming into irrigation.

Salinity problems occur also in non-irrigated croplands and rangelands either as a result of evaporation and transpiration of saline underground water or due to salt input from rainfall. The saline areas of the world consist of salt marshes of the temperate zones, mangrove swamps of the subtropics, and their interior salt marshes adjacent to salt lakes. Saline soils are abundant in semiarid and arid regions, where the amount of rainfall is insufficient for substantial leaching.

Soluble salts accumulating in the soil must be removed periodically by leaching and drainage. But even when proper technology is applied to the soils, they contain salt concentrations which often impair the growth of crop plants of low salt tolerance. Most crop species and cultured woody species either have a relatively low salt tolerance, or their growth is severely inhibited even at low substrate salinity. Salinity is the major nutritional constraint on the growth of wetland rice.

In saline soils, NaCl is usually the dominant salt. There are three major constraints for plant growth on saline substrate (Marschner, 1995, p. 662): (1) water deficit ('drought stress') arising from the low (more negative) water potential of the rooting medium; (2) ion toxicity associated with the excessive uptake of mainly Cl$^-$ and Na$^+$; (3) nutrient imbalance, caused by depression in uptake and/or shoot transport and impaired internal distribution of mineral nutrients, and calcium in particular.

In many fruit trees and herbaceous crop species, ion toxicity is characterized by growth inhibition and injury of foliage (marginal chlorosis and necrosis on mature leaves). These phenomena occur even at low levels of NaCl salination, under which water deficit is not a constraint. Many plant species such as citrus and leguminous suffer from Cl$^-$ toxicity. The species that suffer most from Na$^+$ toxicity are graminaceous such as wheat, sorghum, and rice. Many crop species with relatively low salt tolerance are typical Na$^+$ excluders, and are capable at low and moderate salinity levels of restricting the transport of Na$^+$ into the leaves where it is highly toxic in salt sensitive species. The causes of salt toxicity in cells are inhibition of enzyme reactions and inadequate compartmentalization between cytoplasm and vacuole. There is also increasing support for the hypothesis of Oertli (1968) of salt accumulation in the leaf apoplasm as an important component of salt toxicity, leading to dehydration and turgor loss and death of leaf cells and tissues.

The mechanism of adaptation of plants to saline substrates is based on the principle that salt tolerance can be achieved by salt exclusion or salt inclusion. Differences in the capacity for $Na^+$ and $Cl^-$ exclusion exist between cultivars of different species. For example, the higher salt tolerance of certain cultivars of wheat, barley and citrus is related to a more effective restriction of shoot transport of both $Na^+$ and $Cl^-$. In grapevine, differences in salt tolerance are closely related to the capacity of rootstocks for $Na^+$ and $Cl^-$ exclusion from the shoots. The capacity for $Cl^-$ exclusion seems to be the effect of a major dominant gene and appears to be independent of the ability of $Na^+$ exclusion from the shoot. Mechanisms which restrict excessive $Na^+$ and $Cl^-$ transport to the shoots of plants grown in saline substrates operate at root level (such as membrane properties, anatomical features) and along the pathway from roots to the shoot. It was shown that the stem tissue of certain species can reabsorbe $Na^+$ from the xylem sap in periods of ample root supply. Retranslocation of $Na^+$ from the shoots to the roots may also contribute to low $Na^+$ contents in the shoots of certain species.

SUMMARY OF THE INVENTION

The movement of materials, including ions, in biological systems, particularly into and out of cells and across intracellular membrane barriers, is carried out by membrane proteins called transporters. In order to be integrated into the membrane, these transporters contain several hydrophobic domains, known as transmembrane domains or spans, which span on the membrane. Families of transporters are known with 11 or 12 transmembrane domains such as, for example, NCX1, a mammalian $Na^+/Ca^{2+}$ exchanger that plays a major role in extrusion of $Ca^{2+}$ ions to the extracellular space following excitation (Nicoll et al., 1990).

According to the present invention, we have cloned and characterized an Arabidopsis transporter, herein designated MHX, of the amino acid sequence depicted in FIG. 1, a new member of the 11–12 transmembrane-domain transporter family that is localized in the vacuolar membrane and functions as an electrogenic exchanger of protons with $Mg^{2+}$ and $Zn^{2+}$ ions. The gene encoding MHX is the first gene encoding a $Mg^{2+}/H^+$ or $Zn^{2+}/H^+$ exchanger that has been cloned so far from any organism.

According to the present invention there is provided an isolated DNA molecule comprising a sequence encoding a polypeptide of the 11–12 transmembrane-domain transporter family having a $Mg^{2+}/H^+$ or $Zn^{2+}/H^+$ exchange activity.

The isolated DNA molecule of the invention may be a genomic, complementary or synthetic DNA. In one embodiment, the isolated DNA molecule is the complementary DNA (SEQ ID NOs:1 and 3) depicted in FIG. 2, or the genomic DNA (SEQ ID NO:4) depicted in FIG. 3, from *Arabidopsis thaliana* cv. C-24, coding for the 539-amino acid polypeptide MHX, a member of the 11–12 transmembrane-domain transporter family of the amino acid sequence (SEQ ID NOs: 2 and 3) depicted in FIG. 1. Hydropathy analyses using the Eisenberg, Schwarz, Komarony and Wall method revealed 11 putative transmembrane domains marked bold and underlined in FIG. 4, rendering MHX a member of the 11–12 transmembrane-domain transporter family.

Besides the shown $Mg^{2+}/H^+$ or $Zn^{2+}/H^+$ activity, MHX also has $Fe^{2+}/H^+$ exchange activity and may be expected to have an exchange activity for proton and other divalent cations such as cadmium, and it may also be involved in other processes in plants such as transport of monovalent cations such as sodium.

According to the present invention there is further provided a chimeric DNA molecule capable of expression in plants comprising: (a) a DNA molecule comprising a sequence encoding a polypeptide of the 11–12 transmembrane domain transporter family having a $Mg^{2+}/H^+$ or $Zn^{2+}/H^+$ exchange activity; and (b) DNA sequences capable of enabling the expression of said polypeptide in plant cells.

The DNA sequences of (b) capable of enabling the expression of said polypeptide in plant cells are, for example, a plant promoter and a plant polyadenylation and termination signal sequence at the 3' non-translated region of the gene such as the nopaline synthase (nos) transcription terminator signal, and optionally a short DNA sequence at the 3' end of the promoter for enhanced translation of the mRNA transcribed from the gene such as, for example, the omega (Ω) sequence derived from the coat protein gene of the tobacco mosaic virus (Gallie et al., 1987).

The promoter used according to the invention may be the natural MHX promoter or it is a DNA sequence not existing in nature linked to the MHX gene. The promoter may be a constitutive, organ-specific, tissue-specific, inducible or chimeric promoter. In one preferred embodiment, the promoter is the constitutive 35S promoter of cauliflower mosaic virus (CaMV35S).

According to the present invention there is further provided an expression vector comprising a chimeric DNA molecule of the invention. An example of such a chimeric DNA molecule is the construct depicted in FIG. 5 herein.

According to the present invention there is further provided a transformed plant cell expressing a polypeptide of the 11–12 transmembrane-domain transporter family having a $Mg^{2+}/H^+$ or $Zn^{2+}/H^+$ exchange activity.

According to the present invention there is further provided a transgenic plant whose cells express a DNA molecule comprising a sequence encoding a polypeptide of the 11–12 transmembrane-domain transporter family having a $Mg^{2+}/H^+$ or $Zn^{2+}/H^+$ exchange activity, particularly the MHX protein described herein, shown to have a divalent cation-proton exchange activity. Said transgenic plants are shown herein to have a lower content of sodium as compared with corresponding wild-type plants, and to have a higher dry matter weight upon growth in media with increased calcium levels as compared with corresponding wild-type plants. This makes them suitable for growth in calcareous soils, that are characterized by high calcium content that restrict plant growth.

The characteristics of the transgenic plants of the invention render them better adapted at growing under stress conditions. Thus, these transgenes will have an improved tolerance to stress conditions as compared with corresponding wild-type plants, said stress conditions comprising drought, temperature, mineral excess or deficiency, osmotic, pH, oxidant, chemical, pathogenic and, particularly, high salinity and high-calcium (saline and calcareous soils, respectively) stresses.

BRIEF DESCRIPTION OF THE DRAWINGS

The invention is herein described, by way of example only, with reference to the accompanying drawings, wherein:

FIG. 1 depicts the three-letter amino acid sequence of the MHX protein (SEQ ID NO:2).

FIG. 2 depicts the nucleotide sequence of the cDNA (SEQ ID NO:1) encoding the MHX protein.

FIG. 3 depicts the nucleotide sequence of the genomic DNA (SEQ ID NO:4) from *Arabidopsis thaliana* cv. C-24, coding for the MHX protein.

FIG. 4 depicts the one-letter amino acid sequences of the MHX protein (SEQ ID NO:2) and of the PID:g2529667 protein of Arabidopsis (SEQ ID NO:5) predicted according to an Arabidopsis genomic sequence which is part of locus ATAC002535 (GenBank) defined in the genome project, and the code homology alignment between the two sequences. |: identical amino acid. –: lack of amino acid. The transmembrane domains 1–11 of MHX, as predicted by the Eisenberg, Schwarz, Komarony and Wall method, are indicated by bold underlined letters.

FIG. 5 is a schematic depiction of a chimeric gene of the invention including the strong constitutive CaMV35S promoter, the Ω enhancer of translation, the coding region of the cDNA coding for MHX including the second intron of the genomic DNA and the nopaline synthase (nos) transcription termination and polyadenylation signal (3').

FIG. 6 shows the intracellular localization of MHX in wild-type Arabidopsis plants. Arabidopsis root membranes were extracted and fractionated in sucrose gradient. The fractions (fraction 1=20% sucrose; fraction 13=45% sucrose) were subjected to Western blot analysis with the following antibodies (Ab): MHX-D—affinity-purified Ab against MHX-derived peptide D (SEQ ID NO: 17); MHX-A—affinity-purified Ab against MHX-derived peptide A (SEQ ID NO:16); VM—Ab against the vacuolar membrane marker VM23; PM—Ab against the Arabidopsis plasma membrane marker protein RD-28; ER—Ab against the endoplasmic reticulum yeast BiP protein.

FIG. 7 shows the intracellular localization of MHX in MHX-transgenic tobacco plants. Membranes were extracted from MHX-transgenic tobacco plants, fractionated in sucrose gradients (fraction 1=20% sucrose; fraction 14=45%) and different fractions were subjected to Western blot analysis with the following antibodies (Ab): MHX—affinity-purified Ab against peptide D; VM—monoclonal Ab against the vacuolar membrane marker $H^+$-ATPase; PM—Ab against the plasma membrane $H^+$-ATPase; ER—Ab as in FIG. 6 above.

FIG. 8 shows expression of MHX in control and MHX-transgenic tobacco plants and tobacco cell suspension cultures. Proteins were extracted from control and MHX-transforrned tobacco plants or cultures and were subjected to Western blot analysis with affinity-purified anti-peptide D antibodies. Lane A—MHX-transgenic culture number 1; Lane B—MHX-transgenic culture number 3; Lane C—control non-transformed culture; Lane D—wild-type non-transformed tobacco plant; Lane E—MHX-transgenic tobacco plant number 9; Lane F—MHX-transgenic tobacco plant number 2.

DESCRIPTION OF THE PREFERRED EMBODIMENTS

Figure 9:
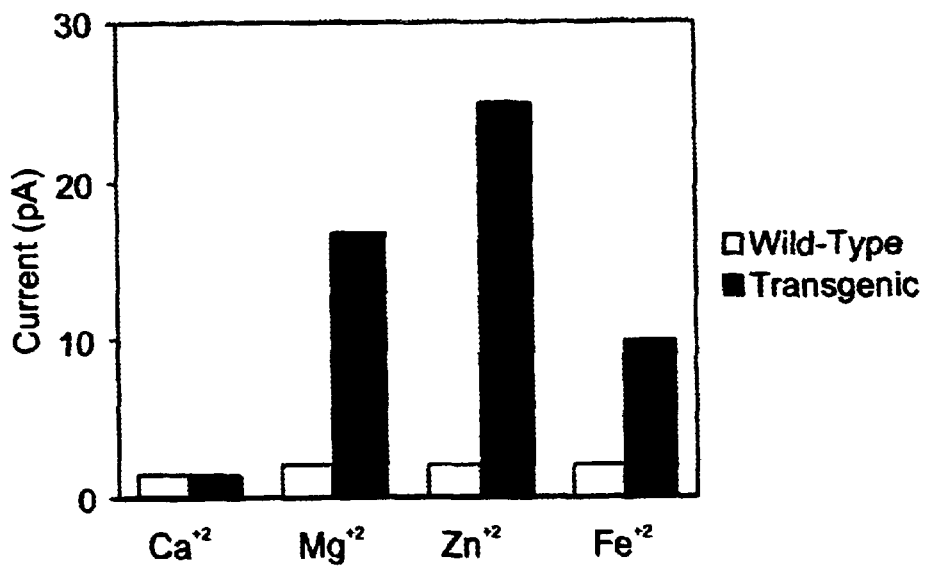
FIG. 9 is a graph showing proton-gradient dependent divalent cation transport in vacuoles of MHX-transformed tobacco BY-2 cells. The transport activity of MHX was examined in vacuoles and in plasma membranes of wild-type and MHX-transformed tobacco BY-2 cell lines. The pipette solution (pH 7.7) included $Mg^{2+}$, $Zn^{2+}$, $Fe^{2+}$ or $Ca^{2+}$. The Figure represent the currents that were measured in vacuoles two seconds after changing the pH of the bath solution from 7.7 to 5.5. Similar currents in the vacuoles of non-transformed cultures were significantly lower. No currents were detectable using this procedure in plasma membranes.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As detailed in the Background section, cellular functions require adequate homeostasis of several divalent metal cations, including $Mg^{2+}$ and $Zn^{2+}$. $Mg^{2+}$, the most abundant free divalent cytoplasmic cation, is essential for many enzymatic reactions, while $Zn^{2+}$ is a structural constituent of various enzymes. Multicellular organisms have to balance not only the intake of $Mg^{2+}$ and $Zn^{2+}$, but also the distribution of these ions to various organs. To date, genes encoding $Mg^{2+}$ transport proteins have not been cloned from any multicellular organism.

The present invention relates to the cloning and characterization of an *Arabidopsis thaliana* transporter, designated MHX, which is localized in the vacuolar membrane and functions as an electrogenic exchanger of protons with $Mg^{2+}$ and $Zn^{2+}$ ions. Functional homologs of MHX have not been cloned from any organism. MHX mRNA is mainly found at the vascular cylinder, and a large proportion of the mRNA is localized in close association with the xylem tracheary elements (not shown). This localization indicates that MHX may control the partitioning of $Mg^{2+}$ and $Zn^{2+}$ between the various plant organs.

According to the present invention, a complementary DNA (SEQ ID NOs: 1 and 3) and a genomic (SEQ ID NO:4) DNA sequences from *Arabidopsis thaliana* cv. C-24 encoding a 539-amino acid transporter protein designated MHX (SEQ ID NOs: 2 and 3) were isolated and characterized. Hydropathy analyses using the Eisenberg, Schwarz, Komarony and Wall method revealed 11 putative and conserved transmembrane domains marked bold and underlined in FIG. 4, rendering MHX a member of the 11–12 transmembrane-domain transporter family.

Biochemical and physiological studies revealed that MHX is a vacuolar membrane protein and that it is a magnesium-proton ($Mg^{2+}/H^+$) exchanger which employs proton ($H^+$) gradient to transport magnesium ions ($Mg^{2+}$) or zinc ions ($Zn^{2+}$) or other divalent ions, such as ferrum ions ($Fe^{2+}$), but not calcium ions ($Ca^{2+}$), against their electrochemical gradient.

The 2803 bp MHX genomic clone was here isolated for the first time according to the present invention. Its sequence is comprised within locus ATAC002535 (GenBank). The suggested translation of the published genomic sequence derived from locus ATAC002535, designated PID:g2529667 (SEQ ID NO:5), includes, as shown in FIG. 4, only 474 amino acids. Compared to the MHX of the present invention, the known sequence lacks the N-terminal 66 amino acids including the initiator methionine and the first transmembrane domain of MHX. Furthermore, it includes a stretch of seven successive non-identical amino acids (marked bold in FIG. 4) of which five successive amino acids are also not conserved within the MHX sequence. This domain in the MHX gene is predicted to be between transmembrane domains 5 and 6 (FIG. 4). Due to its homology to known $Na^+/Ca^{2+}$ exchangers, it was suggested that the PID:g2529667 protein is a putative $Na^+/Ca^{2+}$ exchanger. Since it lacks the terminal 66 amino acids including the first transmembrane domain, it is clear that the PID:g2529667 protein is not functional because it cannot be properly assembled.

As used herein in the specification and in the claims section below, the term "divalent cation-proton exchange activity" refers to the ability to employ proton ($H^+$) gradient to transport divalent cations, such as magnesium ions ($Mg^{2+}$) and other divalent ions, such as zinc ions ($Zn^{2+}$) and ferrum ions ($Fe^{2+}$), against their electrochemical gradient.

According to yet another aspect of the present invention there is provided an expression vector comprising a chimeric DNA molecule of the invention, expressible from the expression vector. Any suitable expression vector for plant transformation can be used according to th invention. In a preferred embodiment, the chimeric gene is cloned into an Agrobacterium binary vector.

As used herein in the specification and in the claims section below, the terms "expressing", "expression" and "expressible" refers to the processes executed by cells while producing proteins, including where applicable, but not limited to, for example, transcription, translation, folding and post-translational modification, processing and transport.

As used herein in the specification and in the claims section below, the term "transformed" refers to the result of a process of inserting nucleic acids into plant cells. The insertion may, for example, be effected by transformation, viral infection, injection, transfection, gene bombardment, electroporation or any other means effective in introducing nucleic acids into plant cells. Following transformation, the nucleic acid is integrated entirely or partially either into the cell's genome (DNA) or remains external to the cell's genome, thereby providing stably transformed or transiently transformed cells.

As used herein in the specification and in the claims section below, the phrase "transformed cell" refers to a cell that includes one or more copies of a recombinant gene.

As used herein in the specification and in the claims section below, the term "transgenic plant" refers to a plant comprised at least partially of transformed cells. It includes also plants resulting, for example, from grafting between a transformed and a nontransformed plant, whereby parts of the resulting plant will be comprised of transformed cells and other parts of nontransformed cells.

Listed hereinunder are some considerations which may be useful in implementing some or all of the above aspects of the present invention.

Optimal uptake and distribution of ions in different soil conditions may be dependent on several different factors such as: (i) level of proton/cation exchange activity; (ii) membrane localization of the exchanger; (iii) expression of the exchanger by special cells; and (iv) modification of the exchanger to improve its transport activity.

The level of the exchanger and hence the level of proton/cation exchange may be altered by using different promoters as well as by using various controlling DNA elements that modulate transcription, post-transcription and translation.

The expression of the DNA molecules employed according to the present invention in plants is carried out under the control of a suitable plant promoter. Promoters which are known or found to cause transcription of selected gene or genes in plant cells can be used according to the invention. The particular promoter selected should be capable of causing sufficient expression to result in the production of an effective amount of the desired protein. Such promoters may be obtained from plants or plant pathogens such as bacteria or viruses.

The promoter can be a constitutive promoter which is active in all or most plant tissues, a tissue- or organ-specific promoter which is active mostly in specific tissue(s) or organ(s), an inducible promoter which is induced under stress conditions, and a chimeric promoter. The phrase "tissue specific promoter" refers also to a developmental stage specific promoter.

There is a plurality of constitutive promoters known to express in plant tissues. Examples of constitutive promoters that can be used according to the invention include, but are not necessarily limited to, the 35S and 19S promoters of cauliflower mosaic virus (CaMV35S and CaMV19S) [Guilley et al., 1982]; the full-length transcript promoter from the figwort mosaic virus (FMV34S) [U.S. Pat. No. 5,512,466] the promoter of cassava vein mosaic virus (CsVMV) [Verdaguer et al., 1996]; the sugarcane bacilliform badnavirus promoter that is active both in monocots and in dicots [Tzafrir et al., 1998]; promoters isolated from plant genes such as Arabidopsis ACT2/ACT8 actin promoter [An et al., 1996]; Arabidopsis ubiquitin UBQ1 promoter, rice actin promoter [McElroy et al., 1990]and barley leaf thionin BTH6 promoter [Holtorf et al., 1995], and promoters obtained from T-DNA genes of *Agrobacterium tumefaciens* such as nopaline and mannopine synthases.

Particularly useful promoters for use in the present invention are tissue- or organ-specific specific promoters such as root, stem, leaf, flower, fruit or seed specific promoters. Examples of fruit or seed specific promoters include the E8, E4, E17 and J49 promoters from tomato [Lincoln and Fischer 1988], as well as the 2A11 promoter described in U.S. Pat. No. 4,943,674. An example of a flower-specific promoter is described in Helariutta et al., 1993.

Examples of root-specific promoters are the promoters of the hemoglobin genes from *Parasponia andersonii* (Bogusz et al., 1990), the promoter of the peroxidase gene from *Arabidopsis thaliana* (Wanapu and Shinmyo, 1996). An example of a root-specific, salinity and dehydration stress inducible promoter, is the promoter of the ARSK1 gene of Arabidopsis thaliana (Hwang and Goodman, 1990).

Stress inducible promoters can also be employed in the present invention including, but not limited to, the light inducible promoter derived from the pea rbcS gene [Coruzzi et al., 1984]; the promoter from the alfalfa rbcS gene [Khoudi et al., 1997]; promoters active in drought, such as DRE promoter or MYC, MYB promoters [Liu et al., 1998; Abe et al., 1997]; a promoter active in high salinity, such as INT, INPS or prxEa [Nelson et al., 1998; Wanapu et al., 1996]; a promoter active under osmotic shock, such as Ha hsp 17.7G4 or RD21 promoters [Coca et al., 1996; Koizumi et al., 1993]; and a promoter active in cases of pathogenicity, such as hsr303J or str246C [Pontier et al., 1998; Perez et al., 1997].

The constitutive, tissue-specific, organ-specific and inducible promoters used for expressing the recombinant protein of this invention may be further modified, if desired, to alter expression characteristics, thus generating chimeric promoters. For example, the CaMV35S promoter may be ligated to a portion of the ssRUBISCO gene which represses the expression of ssRUBISCO in the absence of light, to create a chimeric promoter which is active in leaves but not in roots. As used herein, the terms "CaMV35S", "FMV35S" or to this effect any other promoter include genetic variations of these promoters, e.g., chimeric promoters derived by means of ligation with operator regions, random or controlled mutagenesis, addition or duplication of enhancer sequences, and the like.

For example, for high level constitutive expression, the CaMV35S promoter can be used, while for root or stem specific expression, root- or stem-specific promoters may be used, respectively. Alteration of the level of expression of the exchanger may also be achieved by screening different transgenic genotypes in which the transgene has been inserted into different positions in the genome (position effect). Variable 5' and 3' untranslated regions may be used to control the translation efficiency.

Transport of proteins to various cellular membranes, such as the vacuolar membrane, the plasma membrane, the ER membrane, the mitochondrial membrane, or the chloroplast membrane, is known to occur by special signals present on the transported protein. Thus, modifying or introducing such signals on the MHX polypeptide may enable to localize it on each of the above mentioned membranes. When the exchanger is directed to the plasma membrane, two different functions may be achieved upon expression in different cell types. Expression in the root epidermal or cortex cells, using epidermal or cortex specific promoters, will result in decreased uptake of divalent metals due to transporter-induced export of these metals (using the acidic pH of the apoplasm) outside the cells. Such an approach may prevent uptake of toxic ions. Specific expression of the exchanger in the xylem parenchyma cells (using for instance its own promoter) is expected to increase the loading of divalent ions into the xylem, using the acidic pH of the xylem vessels. This may improve uptake of important metals under conditions of their limitations in the soil.

Reference is now made to the following examples, which together with the above descriptions, illustrate the invention in a non limiting fashion.

EXAMPLES

Example 1

Cloning Arabidopsis MHX complementary and genomic DNA sequences: The MHX complementary DNA sequence was cloned by serendipity while attempting to clone a plant homolog for the Swi4 yeast transcription factor.

A first strand cDNA was prepared from poly(A)$^+$ mRNA purified from *Arabidopsis thaliana* cv. C-24 essentially as described in the protocol provided with the 5' RACE System (catalog No. 8374SA, Gibco BRL).

The resultant single stranded cDNAs pool was employed in a PCR reaction with the following degenerated primers originally designed to clone a plant homolog of the Swi4 yeast transcription factor: Primer 3: 5'-CA(C/T)GA(G/A)AA(G/A)GTICA(G/A)GGIGG-3' (SEQ ID NO:6) and Primer 4: 5'-GCCCA(G/A)TGIA (G/A)IGCIGT(G/A)TG-3'. (SEQ ID NO:7).

Throughout this work PCR mixtures included 1 $\mu$l template DNA (no specific emphasis on DNA concentration); 2 $\mu$l reaction buffer for Vent Polymerase (Supplied by New England Biolabs, Inc.); 1 $\mu$l (0.2 $\mu$g) 5'-primer; 1 $\mu$l (0.2 $\mu$g) 3'-primer; 0.4 $\mu$l of 10 mM dNTP; 0.2 $\mu$l of Vent DNA Polymerase (0.4 units, New England Biolabs, Inc.) and 14.4 $\mu$l H$_2$O.

Throughout this work PCR cycling conditions were: for the first two cycles—2 min, 94° C., 2 min, 50° C., 3 min, 72° C.; for the next 38 cycles—0.5 min, 94° C., 0.5 min, 52° C., 3 min, 72° C.; final extension—10 min, 72° C.

The resulting PCR product of about 730 bp was purified from an agarose gel and ligated into a pGEM-5Zf(+) vector (Promega) that was first bluntly linearized with EcoRV.

Throughout this work, the molecular biology procedures employed were according to standard protocols (e.g., Sambrook et al., 1989), with enzymes from New England Biolabs, Inc., and if required, following the manufacturer's instructions.

The resulting cDNA clone was sequenced. Sequence determinations were performed with vector specific and gene specific primers, using an automated DNA sequencer (Applied Biosystems, model 373A). Each nucleotide was read from at least two independent primers. The cDNA clone, 735 bp long, included an open reading frame that showed low homology to animal $Na^+/Ca^{2+}$ exchangers.

To clone the 5' and 3' regions, the 5' and 3' RACE system of Clontech and Gibco BRL (Life Technologies Inc.) was employed, according to the instruction manual provided therewith.

In a first set of reactions the first strand cDNA pool described above or *Arabidopsis thaliana* cv. C-24 total genomic DNA (prepared from *Arabidopsis thaliana* cv. C-24 according to Sambrook et al., 1989) were used independently as templates for PCR reactions with primers 17 and 18 which were selected according to the terminal ends of the 5' and 3' RACE products. Primer 17: 5'-GGGGGAACGCTTGACCGATTC-3' (SEQ ID NO:8); Primer 18: 5'-CCGGGCCTCCAAAATCATAGT-3' (SEQ ID NO:9).

In a second set of reactions 1 µl of each of the first reactions was used independently as templates, for PCR reactions with nested primers 19 and 20. Primer 19: 5'-CCCGTGATCGGCGTATTGTGA-3' (SEQ ID NO:10); Primer 20: 5'-GCCAACTGCCTTTGAACTTTG-3' (SEQ ID NO: 11).

In a third reaction 1 µl of the second reaction of the genomic DNA was used as template, for PCR reaction with internally nested primers 36 and 37. Primer 36: 5'-ATGCCGCTCACCGAGATATT-3' (SEQ ID NO:12); Primer 37: 5'-TCTTCTACTCATGGGGTTTTTC-3' (SEQ ID NO: 13).

The PCR product including the fill length cDNA (SEQ ID NO:1) was obtained after the second reaction (in between primers 19 and 20). This PCR product was purified from an agarose gel and ligated into the pGEM-5Zf(+) vector (Promega) that was bluntly linearized with EcoRV, to obtain plasmid p218.

The PCR product containing the genomic DNA (SEQ ID NO:4) was obtained after the third reaction (in between primers 36 and 37). This PCR product was purified from agarose gels and ligated it into the pGEM-5Zf(+) vector (Promega) that was bluntly linearized with EcoRV, to obtain plasmid p253.

Comparison of the deduced amino acid sequence of the isolate with proteins from the data bank have shown that the isolate exhibits low sequence homology (36.33 % identity) to animal $Na^+/Ca^{2+}$ exchangers NCX1 (Nicoll et al., 1990). Hydropathy analyses predicted that the new protein would be an integral membrane protein featuring 11 transmembrane domains (see FIG. 4).

Example 2

Construction of plasmids for MHX expression in plants and plant transformations: Plasmid p218 was used as a template for a PCR reaction using primers 42 and 35.

Primer 42: 5'-GGGGTTTGAATAAGTTACCATGGCCTCAATTCTTA-3' (SEQ ID NO:14) introduced an NcoI site at the first ATG codon of the MHX cDNA;

Primer 35: 5'-TCTTCTATATGACGCCTGA AACT-3' (SEQ ID NO:15).

The PCR product was isolated from an agarose gel and was ligated into a pGEM-5Zf(+) vector (Promega) that was bluntly linearized with EcoRV, to yield a plasmid designated p370. The cloning orientation was such that the 5' region of the coding sequence of MHX was close to the T7 promoter region of pGEM-5Zf(+).

Due to the presence of the CaMV35S promoter in the pGEM-5Zf(+) vector which can direct some expression also in bacteria and possibly exert deleterious effect thereupon that can result in selection of mutants, a part of the genomic sequence of MHX including the second intron thereof was introduced into plasmid p370, such that the open reading frame in bacteria was destroyed (see FIG. 5).

To this end, a ClaI—xhoI fragment was excised out of plasmid p370, and replaced with a 300 bp ClaI—XhoI fragment of plasmid p253 which included the second intron of MHX, to yield plasmid p20.

Plasmid pJD330 (5.2 Kb, a kind gift from Dr. D. R. Gallie, Department of Biochemistry, University of California, Riverside, USA) includes the strong constitutive CaMV35S promoter, the Q sequence, the coding region of the glucuronidase (gus) gene, and the nopaline synthase (nos) transcription termination and polyadenylation signal (3').

A NcoI-HincII fragment of plasmid p20, including the entire MHX coding sequence, was isolated and inserted in between NcoI and SmaI sites of pJD330 (replacing the gus coding sequence), to create plasmid p21.

Plasmid p21 was cut with XbaI, and the resulting fragments were blunt-ended using Kienow reaction. The fragment that included the coding sequence of MHX, the CaMV35S promoter, the Ω enhancer of translation at its 5' end, and the nos transcription termination and polyadenylation signal at its 3' end, was cloned into a SmaI site of the Agrobacterium binary vector pGSV4 (Shaul et al., 1996), to yield plasmid p22 (FIG. 5).

Example 3

Intracellular localization of MHX in wild-type and transgenic plants: Anti-MHX polyclonal antibodies were raised in rabbits by standard protocols against two synthetic peptides derived from the MHX sequence, designated peptides A and D. The peptides were linked each through its initial Cys residue to the high-molecular weight KLH carrier (Calbiochem) and injected into rabbits. The antibodies were affinity-purified against the same peptides using the SulfoLink Coupling Gel (Pierce) according to manufacturer's instructions.

Peptide A: Cys Glu Glu Ile Asp Thr Ser Lys Asp Asp Asn Asp Asn Asp Val His Asp (SEQ ID NO:16); and Peptide D: Cys Met Ser Arg Gly Asp Arg Pro Glu Glu Trp Val Pro Glu Glu Ile (SEQ ID NO:17). These peptides corresponded to two regions of predicted non-membranal domains of the MHX sequence.

To identify the intracellular location of MHX in wild-type plants, Arabidopsis root membranes were extracted, fractionated in sucrose gradients as described before (Schaller and DeWitt, 1995), and subjected to Western-blot analysis with the following antibodies (Ab): MHX-D—affimity-purified Ab against MHX-derived peptide D (SEQ ID NO:17); MHX-A—affmity-purified Ab against MHX-derived peptide A (SEQ ID NO:16); VM—Ab against a vacuolar membrane marker [VM23, a homolog of γ-TIP from radish (Raphanus sativus), which is a species closely related to Arabidopsis (Maeshima, 1992), a kind gift from Prof. Maeshima Masayoshi, Laboratory of Biochemistry, Graduate School of Bioagricultural Sciences, Nagoya University, Japan]; PM—Ab against the Arabidopsis plasma membrane marker protein RD-28 (Yamaguchi-Shinozaki et al., 1992), a kind gift of Prof. Chrispeels, M. J. of University of California San Diego; ER—antibodies against the endoplasmic reticulum yeast BiP protein, that specifically recognize plant ER BiP (Shimoni et al., 1995).

As shown in FIG. 6, the two anti-MHXx antibodies A and D recognized a similar band, which co-fractionated with the vacuolar-membrane-marker, and not with either the plasma membrane-marker, or with the ER-marker. These findings indicate that MEX is localized in the vacuole membrane.

To localize the expressed recombinant MHX in transgenic tobacco plants, the experiment was carried out with the following antibodies (Ab): MHX—affinity-purified Ab againt peptide D; VM—monoclonal Ab against the vacuolar membrane marker $H^+$-ATPase (Ward et al., 1992), a kind gift of Dr. Sze Heven, University of Maryland, Maryland, USA; PM—Ab against the plasma membrane $H^+$-ATPase, a kind gift of Dr. Serrano R., University Politecnica de Valencia, Spain; ER—as above.

As shown in FIG. 7, the recombinant MHX protein co-fractionated in sucrose gradients with the vacuolar membrane marker, indicating that most of it was localized in the vacuolar membranes.

Example 4

Expression of MHX in tobacco plants and in tobbaco cell suspension cultures: Plasmid p22 described in Example 2 above was used to transform tobacco cell suspension cultures and tobacco plants, using Agrobacterium-mediated transformation methods. Thus, plasmid p22 was first immobilized into *Agrobacterium tumefaciens* C58C1 (pMP90) (Shaul et al., 1996), using the three-parental-mating procedure (Ditta et al., 1980), and the transformed Agrobacterium was used to transform the tobacco BY-2 cell line (Nagata et al., 1992), kindly provided by the Tobacco Science Research Laboratory, Japan Tobacco Inc., as described before (Shaul et al., 1996) and to transform *Nicotiana tabaccum* cv Samsun NN by the leaf-disk approach as previously described (Horsch et al., 1985).

The transgenic suspension cultures and plants produced a protein with the expected molecular weight of about 53 kD, which crossreacted with the anti-MHX antibodies A and D. Such a protein band was not detected in control, non-transformed cells (FIG. 8).

Example 5

Activity of recombinant MHX: The activity of recombinant MHX was examined in two independently transformed tobacco BY-2 cell lines using the giant-patch clamp technique, as described before (Hilgemann, 1995).

Vacuoles of MHX-transformed cells exhibited a $Mg^{2+}/H^+$, $Zn^{2+}/H^+$ and $Fe^{2+}/H^+$ exchange activity that was significantly higher than that of vacuoles from control non-transformed cells (FIG. 9). This is the first disclosure of a cloned gene encoding a protein with $Mg^{2+}/H^+$ or $Zn^{2+}/H^+$ exchange activity.

$Mg^{2+}/H^+$-derived currents were not detected in the plasma membrane of the transformed cells (data not shown). The MHX exchanger was not able to exchange protons with $Ca^{2+}$ (FIG. 9). The concentration of ions that were tested were 2 mM for $Mg^{2+}$ and $Ca^{2+}$ and 0.2 mM for $Zn^{2+}$ and $Fe^{2+}$.

In all aspects studied in the above examples there was no detectable difference between the 2 independently transformed tobacco BY-2 cell lines.

Example 6

Figure 10:
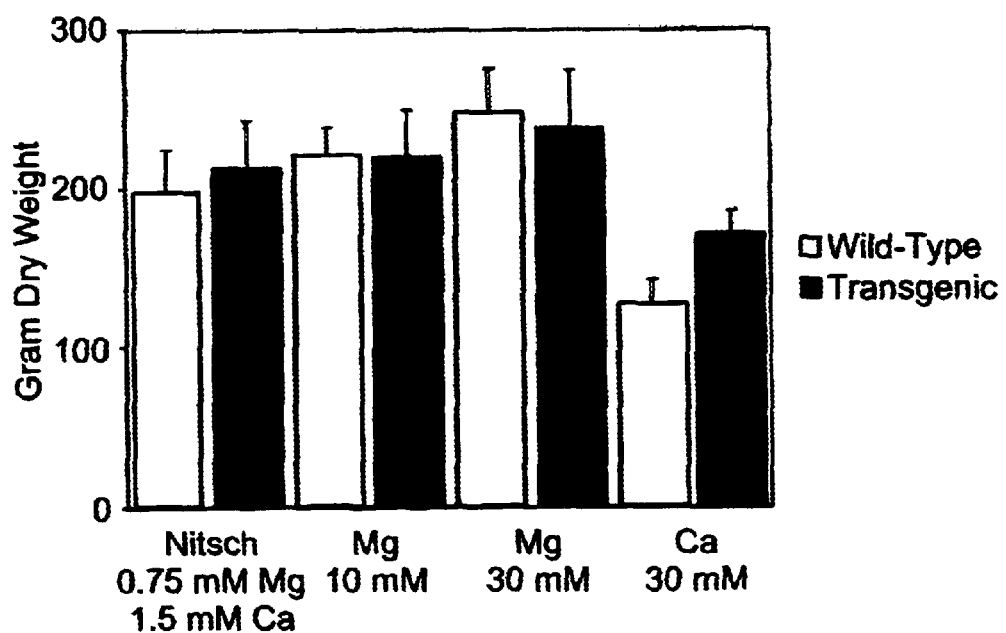
FIG. 10 shows the ameliorating effect of MHX expression on plant growth in the presence of a high calcium concentration. F1 seeds of M-transformed and non-transformed tobacco plants were surface-sterilized and germinated in tissue-culture plates on Nitsch medium including kanamycin as a selective agent. Ten-day old seedling (of which 2:3 were heterozygous and 1:3 homozygous) were transferred with their intact roots into 15 cm diameter plates containing Nitsch medium (that includes 0.75 mM Mg and 1.5 mM Ca) supplemented with either 10 mM $Mg(NO_3)_2$, 30 mM $Mg(NO_3)_2$, or 30 mM $Ca(NO_3)_2$. Each plate included 12 plants of the same genotype (either wild-type or transgenic). For each of the different treatments (the different ion supplementation) 4 plates were prepared of wild-type plants, two plates of transgenic plant genotype 2, and two plates of transgenic plants genotype 9. Differences were not observed between the phenotypes of the transgenic genotypes 2 and 9, and therefore they were treated as a single genotype for the statistical analysis. A month later, all the aerial parts of the plants were excised from each plate and the total dry weight of the plants derived from each of the plates was determined. Each column represents the average and the standard deviation of 4 plates, of either the wild-type or the transgenic plants. The growth of both wild-type and transgenic plants grown in the presence of 30 mM Ca was significantly inhibited compared to plants grown on Nitsch medium containing 1.5 mM Ca, but the transgenic plants were significantly less inhibited. The difference between the dry weight of the transgenic and wild-type plants that were grown on the high calcium medium were significant ($p<0.05$), as indicated by the Anova test.
Figure 11A:
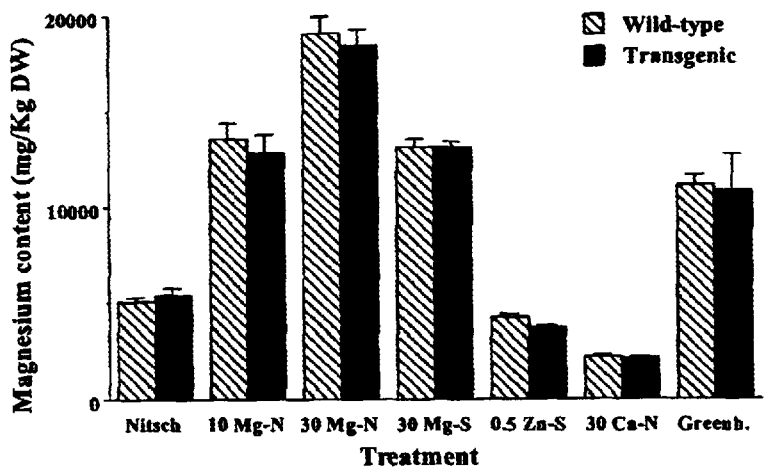
FIGS. 11A–E show the magnesium, zinc, calcium, sodium and potassium content, respectively, in shoots of MHX-transformed and non-transformed plants. For plants grown in tissue culture, F1 seeds of transformed and non-transformed tobacco plants were surface-sterilized and germinated in tissue-culture plates on Nitsch medium including kanamycin as a selective agent. Ten-day old seedling (of which 2:3 were heterozygous and 1:3 homozygous) were transferred with their intact roots into 15 cm diameter plates containing Nitsch medium supplemented with various minerals (Mg, Zn, Ca) as indicated in FIGS. 11A–E. The plants were grown further for 1 month. Then all their aerial parts were cut, washed twice in double-distilled water, and their mineral content was determined. For the wild-type plants, each column represents the average of 4 plates (each plate included 12 seedlings). For the transgenic plants, each column represents the average of 4 plates, of which each 2 plates were of the two transgenic genotypes 2 and 9. These two genotypes had a similar level of MHX expression and similar mineral content. For plants grown in the greenhouse, seeds of homozygous transgenic plants were grown in soil until the plants were 50 cm long. Their lower leaves were cut, washed twice with double-distilled water, and analyzed. Each column represents the average of 2 different plants (of the two different genotypes 2 and 9 for the transgenic plants). Except plants grown in the greenhouse (Greenh.), all the plants were grown in Nitsch medium containing standard levels of $Mg^{2+}$ (0.75 mM $Mg_2SO_4$), $Zn^{2+}$ (0.035 mM $Zn_2SO_4$), and $Ca^{2+}$ (1.5 mM $CaCl_2$) or supplemented with the indicated levels (in mM) of cations. The accompanying anions were either nitrate (N) or sulfate (S).
Figure 11B:
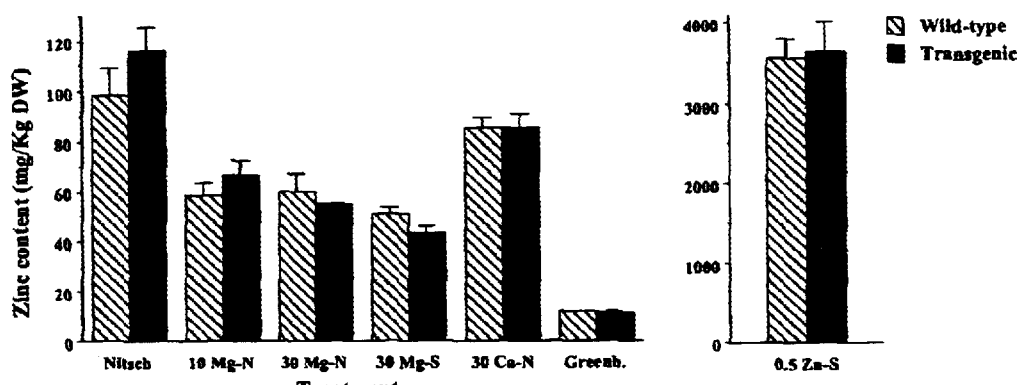
Figure 11C:
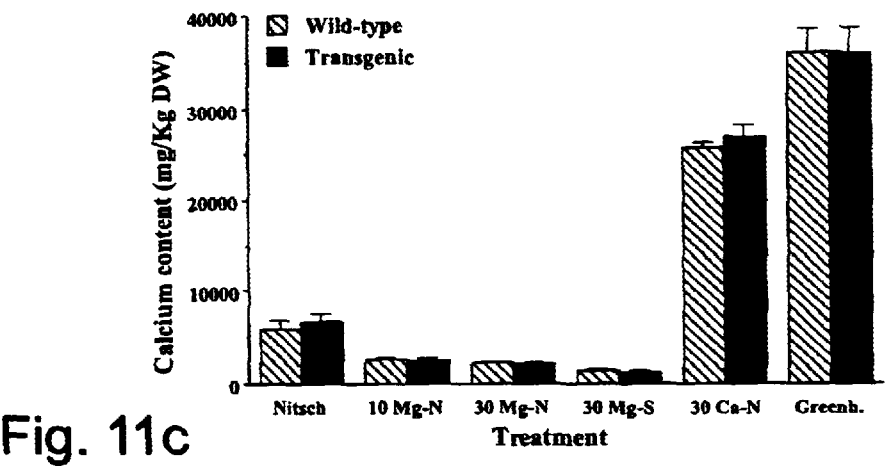
Figure 11D:
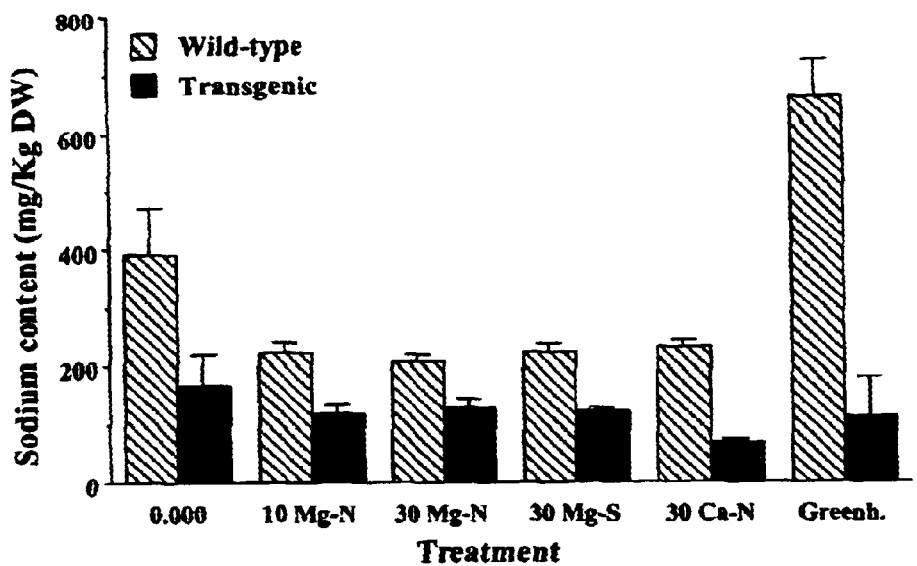
Figure 11E:
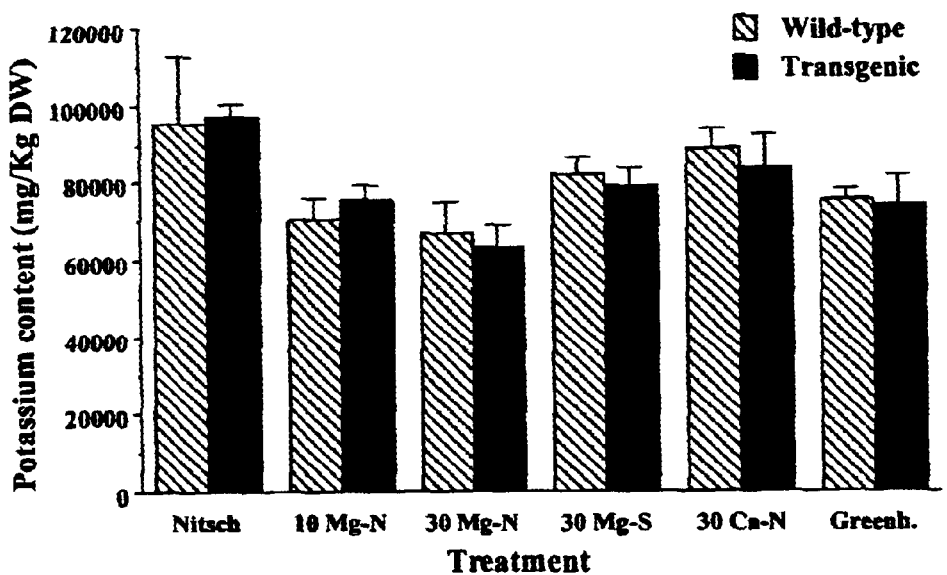

Growth of transgenic plants expressing MHX in the presence of high Mg or Ca levels in the growth medium: Wild-type and MHX-transformed plants were grown on Nitsch medium including 10 mM $Mg(NO_3)_2$, 30 mM $Mg(NO_3)_2$ or 30 mM $Ca(NO_3)_2$. As shown in FIG. 10, the growth of both wild-type and transgenic plants was not inhibited in the presence of high Mg levels. In contrast, the growth of both wild-type and transgenic plants was inhibited in the presence of 30 mM $Ca(NO_3)_2$ as compared to plants grown on Nitsch medium containing 1.5 mM $Ca^{2+}$, but the transgenic plants were significantly less inhibited. This indicates the potential of MHX production in transgenic plants to overcome the problem of growing plants in the presence of high levels of Ca in the medium or soil.

Example 7

Effect of MHX expression in accumulation of cations in plants: To test whether MHX expression affects the accumulation of cations in the MHX-transformed plants, we measured the amounts of various cations in shoots of transforrned and non-transformed plants grown with normal as well as in elevated $Mg^{2+}$, $Zn^{2+}$ or $Ca^{2+}$ levels.

For the mineral content analysis, the plant material was dried 48 hours in a 70° C. oven, and then crushed into a fine powder. For each sample, 120–250 mg dry powder were weighed into 50 ml polypropylene disposable test tubes, and 5 ml of concentrated nitric acid were added. Ten samples were processed at a time. The tubes were left unsealed for 10 min and then were fitted with a screw cap that was left untightened. The tubes, in a plastic stand, were transferred to a temperature controlled microwave oven (an MLS 1200 mega microwave digestion unit, Milestone Sorisole (BG) Italy). The samples were subjected to three digestion cycles of 20 min each, at 450 W of microwave power and 95° C. The vessels were allowed to cool for 10 min between cycles, and were finally brought to room temperature and were uncapped. The volume was made up to 25 ml with deionized water. Analyses were conducted on portions of these solutions. $Na^+$ and $Ca^{2+}$ content were determined by inductively coupled plasma atomic emission spectrometry. An ICP-AES, model "Spectroflame" from Spectro, Kleve, Germany was used.

As shown in FIG. 11, the amounts of magnesium, zinc or calcium increased in shoots of plants grown in media containing elevated levels of these minerals. However, no difference was observed in the total content of these cations between shoots of transformed and non-transformed plants. Unexpectedly, we found that the MHX-transgenic plants have significantly less sodium in their shoots compared to wild-type plants. The levels of several other cations and minerals analyzed (potassium, cupric, ferrum, silicon, manganese, barium, strontium, molybdenum, selenium, boron, sulfate, phosphate) were essentially similar in leaves of wansformed and non-transformed plants (FIG. 11 and data not shown).

Salinity stress has many causes and it is generally assumed that it will not be overcome by a single genetic modification (Serrano, 1996). The MHX genetic modification may contribute to salt tolerance. As detailed in the Background section, one of the constraints exerted by salinity stress is sodium toxicity, brought about by high levels of sodium in the shoots; accordingly, many salt-tolerant species developed mechanisms for restricting sodium transport to the shoots (Marschner, 1995, pp. 84–85). The reduced sodium levels in the shoots of transgenic plants expressing MHX may reduce sodium ion toxicity and thus may increase salt tolerance in the transgenic plants. There is no direct explanation how MHX expression reduces sodium content in the leaves. Although MHX has been characterized by our electrophysiological analyses as an exchanger of protons with $Mg^{2+}$, $Zn^{2+}$ and $Fe^{2+}$ ions, we cannot exclude the possibility that under some conditions $Na^+$ ions are able to compete with either the protons or the divalent cations.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

REFERENCES

1. Abe, H. et al.,(1997) *Plant Cell*, 9: 1859–68.
2. Amalou, Z., Gibrat, R, Brugidou, C., Trouslot, P. and d'Auzac, J. (1992) Evidence for an amiloride-inhibited $Mg^{2+}/2H^+$ antiporter in lutoid (vacuolar) vesicles from latex of *Hevea brasiliensis*. *Plant Physiol.*, 100: 255–260.
3. Amalou, Z., Gibrat, R., Trouslot, P. and d'Auzac, J. (1994) Solubilization and reconstitution of the $Mg^{2+}/2H^+$ antiporter of the lutoid tonoplast from *Hevea brasiliensis* latex. *Plant Physiol.*, 106: 79–85.
4. An, Y. Q. et al., (1996) *Plant J.*, 10: 107–21.
5. Bogusz, D. et al., (1990) *Plant Cell*, 2: 633–641.
6. Coca, M. A. et al., (1996) *Plant Mol Biol.*, 31: 863–76.
7. Conruzzi, G. et al., (1984) *EMBO J.*, 3: 1671–1679.
8. Ditta, G., Stanfield, D., Corbin, D. and Helinski, D., R. (1980) *Proc. Natl. Acad. Sci. USA* 77, 7347.
9. Eisenberg, D., Schwarz, E., Komaromy, M. and Wall, R. (1984) Analysis of membrane and surface protein sequences with the hydrophobic moment plot *J. Mol. Biol.*, 179: 125–142.
10. Gallie, D. R., Sleat, D. E., Watts, J. W., Turner, P. C. and Wilson, T. M. (1987) The 5'-leader sequence of tobacco mosaic virus RNA enhances the expression of foreign gene transcripts in vitro and in vivo. *Nuc. Acid Res.*, 15: 3257–3273.
11. Guilley, H. (1982) Transcription of Cauliflower mosaic virus DNA: detection of promoter sequences, and characterization of transcripts. *Cell*, 30: 763–773.
12. Gunshin H., Mackenzie, B., Berger, U. V., Gunshin, Y., Romero, M. F., Boron, W. F., Nussberger, S., Gollan J. L. and Hediger, M. A. (1997) Cloning and characterization of a mammalian proton-coupled metal-ion transporter. *Nature*, 388: 482–488.
13. Helariutta, Y. et al., (1993) Cloning of cDNA for dihydroflavonol-4-reductase (DFR) and characterization of dfr expression in the corollas of Gerbera hybrida var. Regina (Compositae). *Plant Mol. Biol.*, 22: 183–193.
14. Hilgemann, D. W. (1995) The Giant Membrane Patch. In Sakmann, B. and Neher, E. (eds.), *Single-Channel Recording*. Plenum Press, New York, pp. 307–327.
15. Hmiel, S. P., Snavely, M. D., Florer, J. B., Maguire, M. E. and Miller, C. G. (1989) Magnesium transport in *Salmonella typhimurium*: genetic characterization and cloning of three magnesium transport loci. *J. Bacteriol.*, 171: 4742–4751.
16. Holtorf, S. et al., (1995) *Plant Mol Biol.*, 29:637–46;
17. Horsch, R. B., Fry, J. E., Hoffmann, N. L., Eichholtz, D., Rogers, S. G. and Fraley, R. T. (1985) A simple and general method for transferring genes into plants. *Science*, 227: 1229–1231.
18. Hwang, I. and Goodman, H. M. (1995) An Arabidopsis thaliana root-specific kinase homolog is induced by dehydration, ABA, and NaCl. *Plant J.*, 8: 3743.
19. Khoudi et al., (1997) *Gene*, 197: 343–351.
20. Koizumi, M. et al., (1993) Gene, 129: 175–82.
21. Lincoln, J. and Fischer, R. (1988) Diverse mechanisms for the regulation of ethylene-inducible gene expression. *Mol Gen Genet.*, 212: 71–75.
22. Liu, X. and Gorovsky, M. A. (1993) Mapping the 5' and 3' ends of *Tetrahymena thermophila* mRNAs using RNA ligase mediated amplification of cDNA ends (RLM-RACE). *Nuc. Acids. Res.*, 21: 4954–4960.
23. Liu, Q. et al., (1998) *Plant Cell*, 10: 1391–406.
24. Maeshirna, M. (1992) Characterization of the major integral protein of vacuolar membrane. *Plant Physiol.*, 98: 1248–1254.
25. Marschner, H. (1995) *Mineral nutrition of higher plants*. Academic Press, London.
26. McElroy, D. et al., (1990) *The Plant Cell*, 2: 163–171.
27. Nagata, T., Nemoto, Y. and Hasezawa, S. (1992) Tobacco BY-2 cell line as the "HeLa" cell in the cell biology of higher plants. *Int. Rev. Cytol.*, 132: 1–30.
28. Nelson, D. E. et al., (1998) *Plant Cell*, 10: 753–64.
29. Nicoll, D. A., Longoni, S. and Philipson. K. D. (1990) Molecular cloning and functional expression of the cardiac sarcolemmal $Na^+/Ca^{2+}$ exchanger *Science*, 250: 562–565.
30. Nitsch, J. P. (1969) Experimental androgenesis in *Nicotiana. Phytomorph.*, 19: 389–404.
31. Oertli, J. J. (1968) Extracellular salt accumulation, a possible mechanism of salt injury in plants. Agrochimica, 12: 461469.
32. Perez, V. et al., (1997) *Mol Plant Microbe interact.* 10: 750–60.
33. Pfeiffer, W. and Hager, A. (1993) A $Ca^{2+}$-ATPase and a $Mg^{2+}/H^+$-antiporter are present on tonoplast membranes from roots of *Zea mays* L. *Planta*, 191: 377–385.
34. Pontier, D. et al., (1998) *Mol Plant Microbe interact.* 11: 544–54.
35. Rensing, C., Mitra, B. and Rosen, B. P. (1997) The znta gene of *Escherichia coli* encodes a Zn(II)-translocating P-type ATPase. *Proc. Natl. Acad. Sci. USA*, 94: 14326–14331.
36. Sambrook, J., Fritsch, E. F. and Maniatis, T. (1989) Molecular cloning—a *laboratory manual*. Cold Spring Harbor Laboratory Press.
37. Schaller, G. E. and DeWitt, N. D. (1995) Analysis of the $H^+$-ATPase and other proteins of the Arabidopsis plasma membrane. *Methods Cell Biol.*, 50: 129–148.
38. Serrano, R. (1996) Salt tolerance in plants and microorganisms: toxicity targets and defense responses. *Int. Rev. Cyt.*, 165: 1–52.
39. Shaul, O., Mironov, V., Burssens, S., Van Montagu, M. and Inzé, D. (1996) Two Arabidopsis cyclin promoters mediate distinctive transcriptional oscillation in synchronized tobacco BY-2 cells. *Proc. Natl. Acad Sci. USA*, 93: 4868–4872.
40. Shimoni, Y., Zhu, X., Levanony, H., Segal, G. and Galili, G. (1995) Purification, characterization, and intracellular localization of glycosylated protein disulfide isomerase from wheat grains. *Plant Physiol.*, 108: 327–335.
41. Smith, R. L., Banks, J. L., Marshall, D. S. and Maguire, M. E. (1993) Sequence and topology of the CorA magnesium transport systems of *Salmonella typhimurium* and *Escherichia coli*. Identification of a new class of transport proteins. *J. Biol. Chem.*, 268: 14071–14080.
42. Smith, R. L., Mompson, L. J. and Maguire, M. E. (1995) Cloning and characterization of mgtE, a putative new class of Mg$^{2+}$ transporter from *Bacillus firmus* OF4. *J. Bacteriol.*, 177: 1233–1238.
43. Tzafrir, I. et al., (1998) *Plant Mol Biol.*, 38: 347–56.
44. Verdaguer, B. et al., (1996) *Plant Mol Biol.*, 31: 1129–39.
45. Wanapu, C. and Shinmyo, A. (1996) cis-regulatory elements of the peroxidase gene in Arabidopsis thaliana involved in root-specific expression and responsiveness to high-salt stress. *Ann NY Acad Sci.* 782: 107–14.
46. Ward, J. A., Reinders, H. H. and Sze, H. (1992) Dissociation and reassembly of the vacuolar H$^+$-ATPase complex from oat roots. *Plant Physiol.* 99: 161–169.
47. Yamaguchi-Shinozaki, K., Masahiro, K., Satomi, U. and Kazuo, S. (1992) Molecular cloning and characterization of 9 cDNAs for genes that are responsive for desiccation in *Arabidopsis thaliana*: sequence analysis of one cDNA clone that encodes a putative transmembrane channel protein. *Plant Cell Physiol.*, 33: 217–224.
48. Zhao, H. and Eide, D. (1996a) The yeast ZRT1 gene encodes the zinc transporter protein of a high-affinity uptake system induced by zinc limitation. *Proc. Natl. Acad. Sci. USA*, 93: 2454–2458.
49. Zhao, H. and Eide, D. (1996b) The ZRT2 gene encodes the low affinity zinc transporter in *Saccharomyces cerevisiae. J. Biol. Chem.*, 271: 23203–23210.

What is claimed is:

1. A transformed plant cell expressing a recombinant polypeptide as set forth in SEQ ID NO: 2.

2. A transgenic plant comprising the transformed plant cell of claim 1.

3. The transgenic plant of claim 2, wherein the transgenic plant is characterized by a higher dry matter weight when grown in calcium-rich media as compared with a corresponding wild-type plant grown under identical conditions.

4. The transformed plant cell of claim 1, wherein said recombinant polypeptide is encoded by a nucleic acid molecule set forth in SEQ ID NO: 1 or 4.

\* \* \* \* \*

SEQUENCE LISTING

<160> NUMBER OF SEQ ID NOS: 17

<210> SEQ ID NO 1
<211> LENGTH: 1950
<212> TYPE: DNA
<213> ORGANISM: Arabidopsis thaliana

<400> SEQUENCE: 1

```
tcgatttccg tttgtcggaa aatctctccc gtgatcggcg tattgtgaat gccgctcacc      60
gagatattct ccgattcttt tccccagtga ggacaagtgt tcagttgact tattaggagg     120
tggggtttga ataagttaca atggcctcaa ttcttaatca aacccaggag ttgcaagaat     180
cttctaaggt tcttgggcat ttaagatgtg aaaacttctt tctattcccc ggagaaaaca     240
ctttgtcaga tggtttgagg ggtgtgttat attttctcgg tcttgcctac tgctttattg     300
ggttgtcagc catcactgca cggttcttca agtctatgga gaatgtcgtg aaacattccc     360
gtaaagtggt tacaattgat cccattacta aagctgaagt catcacatac aagaaagttt     420
ggaactttac tattgcagac atcagtttgt tggcgtttgg aactagcttc cctcagattt     480
ctttggctac catcgatgca atacggaata tgggggagcg gtatgctgga ggtcttggtc     540
ctggaacact tgttggctca gctgcatttg atcttttccc catccacgct gtttgtgtcg     600
ttgtgccaaa agctggagaa ctgaaaaaga tatccgactt aggtgtttgg ctagttgagc     660
tcgtatggtc tttttgggct tacatctggc tatacataat cctcgaggtg tggtcaccaa     720
acgtaattac acttgtggag gcattattga cagtactgca atacggattg cttctagttc     780
atgcgtacgc ccaagacaag cgatggcctt acttgtcttt accaatgtca agaggtgata     840
ggccagagga gtgggttcca gaggagattg atacatccaa agatgacaat gacaatgatg     900
ttcatgatgt gtattcggat gctgctcaag atgctgttga atcgggaagc agaaacattg     960
ttgatatctt ctctattcat tcagctaaca atgatacagg gatcacttat catactgtgg    1020
cagatactcc acccgattct gcgactaaga agggtaaggc gaagaattct actgttttg     1080
acatttggaa acatcaattc gtggatgcaa taacgttgga aacatcagaa tcaaagaaag    1140
tggatagcat ttatcttcga atcgcgaaat ctttctggca tttactcctc gccccttgga    1200
aactgctttt tgcatttgtg ccccctgca acattgctca cggttggatc gctttcatct    1260
gctctctcct cttcatcagt ggagtagcct ttgttgtcac aagatttact gaccttataa    1320
gctgtgtcac tggaataaac ccatatgtga tagcattcac agcactcgca agtggaactt    1380
catggccaga cttagtagca agtaaaatcg ctgcagagcg acaactaacc gcagattcag    1440
ctattgcaaa catcacctgc agtaactcgg tgaacatcta tgtggggatt ggagttccgt    1500
ggctgataaa cacagtctac aactactttg catacagaga gcctttatac atagaaaacg    1560
```

-continued

```
ctaaaggatt aagcttttcg cttctgatat tctttgcgac atcagtggga tgtatcgtgg    1620
tgcttgtgtt gagaaggttg attataggag ctgagcttgg aggtccaagg ctatgggctt    1680
ggcttacttc tgcctatttc atgatgcttt gggtcgtctt cgttgttctt tcttctttga    1740
aagtttcagg cgtcatatag aagaagcaac aaaaggaaaa accccatgag tagaagaaaa    1800
agtcttagct tacttgcaca tgtctcagtt tttgttttc ttacttgtta aggggtttt      1860 atataattat caaagttcaa aggcagttgg ctaaatatgt gttgcaaata taatcatat     1920 tgactatgat tttggaggct taaaaaaaaa                                      1950
```

<210> SEQ ID NO 2
<211> LENGTH: 539
<212> TYPE: PRT
<213> ORGANISM: Arabidopsis thaliana

<400> SEQUENCE: 2

```
Met Ala Ser Ile Leu Asn Gln Thr Gln Glu Leu Gln Glu Ser Ser Lys
1               5                   10                  15

Val Leu Gly His Leu Arg Cys Glu Asn Phe Phe Leu Phe Pro Gly Glu
            20                  25                  30

Asn Thr Leu Ser Asp Gly Leu Arg Gly Val Leu Tyr Phe Leu Gly Leu
        35                  40                  45

Ala Tyr Cys Phe Ile Gly Leu Ser Ala Ile Thr Ala Arg Phe Phe Lys
    50                  55                  60

Ser Met Glu Asn Val Val Lys His Ser Arg Lys Val Val Thr Ile Asp
65                  70                  75                  80

Pro Ile Thr Lys Ala Glu Val Ile Thr Tyr Lys Lys Val Trp Asn Phe
                85                  90                  95

Thr Ile Ala Asp Ile Ser Leu Leu Ala Phe Gly Thr Ser Phe Pro Gln
            100                 105                 110

Ile Ser Leu Ala Thr Ile Asp Ala Ile Arg Asn Met Gly Glu Arg Tyr
        115                 120                 125

Ala Gly Gly Leu Gly Pro Gly Thr Leu Val Gly Ser Ala Ala Phe Asp
    130                 135                 140

Leu Phe Pro Ile His Ala Val Cys Val Val Pro Lys Ala Gly Glu
145                 150                 155                 160

Leu Lys Lys Ile Ser Asp Leu Gly Val Trp Leu Val Glu Leu Val Trp
                165                 170                 175

Ser Phe Trp Ala Tyr Ile Trp Leu Tyr Ile Ile Leu Glu Val Trp Ser
            180                 185                 190

Pro Asn Val Ile Thr Leu Val Glu Ala Leu Leu Thr Val Leu Gln Tyr
        195                 200                 205

Gly Leu Leu Val His Ala Tyr Ala Gln Asp Lys Arg Trp Pro Tyr
    210                 215                 220

Leu Ser Leu Pro Met Ser Arg Gly Asp Arg Pro Glu Glu Trp Val Pro
225                 230                 235                 240

Glu Glu Ile Asp Thr Ser Lys Asp Asp Asn Asp Val His Asp
                245                 250                 255

Val Tyr Ser Asp Ala Ala Gln Asp Ala Val Glu Ser Gly Ser Arg Asn
            260                 265                 270

Ile Val Asp Ile Phe Ser Ile His Ser Ala Asn Asn Asp Thr Gly Ile
        275                 280                 285

Thr Tyr His Thr Val Ala Asp Thr Pro Pro Asp Ser Ala Thr Lys Lys
    290                 295                 300
```

```
Gly Lys Ala Lys Asn Ser Thr Val Phe Asp Ile Trp Lys His Gln Phe
305                 310                 315                 320

Val Asp Ala Ile Thr Leu Glu Thr Ser Glu Ser Lys Lys Val Asp Ser
            325                 330                 335

Ile Tyr Leu Arg Ile Ala Lys Ser Phe Trp His Leu Leu Ala Pro
            340                 345                 350

Trp Lys Leu Leu Phe Ala Phe Val Pro Pro Cys Asn Ile Ala His Gly
        355                 360                 365

Trp Ile Ala Phe Ile Cys Ser Leu Leu Phe Ile Ser Gly Val Ala Phe
        370                 375                 380

Val Val Thr Arg Phe Thr Asp Leu Ile Ser Cys Val Thr Gly Ile Asn
385                 390                 395                 400

Pro Tyr Val Ile Ala Phe Thr Ala Leu Ala Ser Gly Thr Ser Trp Pro
                405                 410                 415

Asp Leu Val Ala Ser Lys Ile Ala Ala Glu Arg Gln Leu Thr Ala Asp
                420                 425                 430

Ser Ala Ile Ala Asn Ile Thr Cys Ser Asn Ser Val Asn Ile Tyr Val
            435                 440                 445

Gly Ile Gly Val Pro Trp Leu Ile Asn Thr Val Tyr Asn Tyr Phe Ala
    450                 455                 460

Tyr Arg Glu Pro Leu Tyr Ile Glu Asn Ala Lys Gly Leu Ser Phe Ser
465                 470                 475                 480

Leu Leu Ile Phe Phe Ala Thr Ser Val Gly Cys Ile Val Val Leu Val
                485                 490                 495

Leu Arg Arg Leu Ile Ile Gly Ala Glu Leu Gly Gly Pro Arg Leu Trp
                500                 505                 510

Ala Trp Leu Thr Ser Ala Tyr Phe Met Met Leu Trp Val Val Phe Val
            515                 520                 525

Val Leu Ser Ser Leu Lys Val Ser Gly Val Ile
        530                 535

<210> SEQ ID NO 3
<211> LENGTH: 1935
<212> TYPE: DNA
<213> ORGANISM: Arabidopsis thaliana
<220> FEATURE:
<221> NAME/KEY: CDS
<222> LOCATION: (136)..(1755)

<400> SEQUENCE: 3
ttccgtttgt cggaaaatct ctcccgtgat cggcgtattg tgaatgccgc tcaccgagat      60
attctccgat tcttttcccc agtgaggaca agtgttcagt tgacttatta ggaggtgggg     120
tttgaataag ttaca atg gcc tca att ctt aat caa acc cag gag ttg caa     171
               Met Ala Ser Ile Leu Asn Gln Thr Gln Glu Leu Gln
                 1               5                  10 gaa tct tct aag gtt ctt ggg cat tta aga tgt gaa aac ttc ttt cta     219
Glu Ser Ser Lys Val Leu Gly His Leu Arg Cys Glu Asn Phe Phe Leu
        15                  20                  25 ttc ccc gga gaa aac act ttg tca gat ggt ttg agg ggt gtg tta tat     267
Phe Pro Gly Glu Asn Thr Leu Ser Asp Gly Leu Arg Gly Val Leu Tyr
    30                  35                  40 ttt ctc ggt ctt gcc tac tgc ttt att ggg ttg tca gcc atc act gca     315
Phe Leu Gly Leu Ala Tyr Cys Phe Ile Gly Leu Ser Ala Ile Thr Ala
45                  50                  55                  60 cgg ttc ttc aag tct atg gag aat gtc gtg aaa cat tcc cgt aaa gtg     363
Arg Phe Phe Lys Ser Met Glu Asn Val Val Lys His Ser Arg Lys Val
```

```
                     65                  70                   75
gtt aca att gat ccc att act aaa gct gaa gtc atc aca tac aag aaa       411
Val Thr Ile Asp Pro Ile Thr Lys Ala Glu Val Ile Thr Tyr Lys Lys
             80                  85                  90 gtt tgg aac ttt act att gca gac atc agt ttg ttg gcg ttt gga act       459
Val Trp Asn Phe Thr Ile Ala Asp Ile Ser Leu Leu Ala Phe Gly Thr
         95                 100                 105 agc ttc cct cag att tct ttg gct acc atc gat gca ata cgg aat atg       507
Ser Phe Pro Gln Ile Ser Leu Ala Thr Ile Asp Ala Ile Arg Asn Met
        110                 115                 120 ggg gag cgg tat gct gga ggt ctt ggt cct gga aca ctt gtt ggc tca       555
Gly Glu Arg Tyr Ala Gly Gly Leu Gly Pro Gly Thr Leu Val Gly Ser
125                 130                 135                 140 gct gca ttt gat ctt ttc ccc atc cac gct gtt tgt gtc gtt gtg cca       603
Ala Ala Phe Asp Leu Phe Pro Ile His Ala Val Cys Val Val Val Pro
                145                 150                 155 aaa gct gga gaa ctg aaa aag ata tcc gac tta ggt gtt tgg cta gtt       651
Lys Ala Gly Glu Leu Lys Lys Ile Ser Asp Leu Gly Val Trp Leu Val
            160                 165                 170 gag ctc gta tgg tct ttt tgg gct tac atc tgg cta tac ata atc ctc       699
Glu Leu Val Trp Ser Phe Trp Ala Tyr Ile Trp Leu Tyr Ile Ile Leu
        175                 180                 185 gag gtg tgg tca cca aac gta att aca ctt gtg gag gca tta ttg aca       747
Glu Val Trp Ser Pro Asn Val Ile Thr Leu Val Glu Ala Leu Leu Thr
        190                 195                 200 gta ctg caa tac gga ttg ctt cta gtt cat gcg tac gcc caa gac aag       795
Val Leu Gln Tyr Gly Leu Leu Leu Val His Ala Tyr Ala Gln Asp Lys
205                 210                 215                 220 cga tgg cct tac ttg tct tta cca atg tca aga ggt gat agg cca gag       843
Arg Trp Pro Tyr Leu Ser Leu Pro Met Ser Arg Gly Asp Arg Pro Glu
                225                 230                 235 gag tgg gtt cca gag gag att gat aca tcc aaa gat gac aat gac aat       891
Glu Trp Val Pro Glu Glu Ile Asp Thr Ser Lys Asp Asp Asn Asp Asn
            240                 245                 250 gat gtt cat gat gtg tat tcg gat gct gct caa gat gct gtt gaa tcg       939
Asp Val His Asp Val Tyr Ser Asp Ala Ala Gln Asp Ala Val Glu Ser
        255                 260                 265 gga agc aga aac att gtt gat atc ttc tct att cat tca gct aac aat       987
Gly Ser Arg Asn Ile Val Asp Ile Phe Ser Ile His Ser Ala Asn Asn
        270                 275                 280 gat aca ggg atc act tat cat act gtg gca gat act cca ccc gat tct      1035
Asp Thr Gly Ile Thr Tyr His Thr Val Ala Asp Thr Pro Pro Asp Ser
285                 290                 295                 300 gcg act aag aag ggt aag gcg aag aat tct act gtt ttt gac att tgg      1083
Ala Thr Lys Lys Gly Lys Ala Lys Asn Ser Thr Val Phe Asp Ile Trp
                305                 310                 315 aaa cat caa ttc gtg gat gca ata acg ttg gaa aca tca gaa tca aag      1131
Lys His Gln Phe Val Asp Ala Ile Thr Leu Glu Thr Ser Glu Ser Lys
            320                 325                 330 aaa gtg gat agc att tat ctt cga atc gcg aaa tct ttc tgg cat tta      1179
Lys Val Asp Ser Ile Tyr Leu Arg Ile Ala Lys Ser Phe Trp His Leu
        335                 340                 345 ctc ctc gcc cct tgg aaa ctg ctt ttt gca ttt gtg ccc ccc tgc aac      1227
Leu Leu Ala Pro Trp Lys Leu Leu Phe Ala Phe Val Pro Pro Cys Asn
        350                 355                 360 att gct cac ggt tgg atc gct ttc atc tgc tct ctc ctc ttc atc agt      1275
Ile Ala His Gly Trp Ile Ala Phe Ile Cys Ser Leu Leu Phe Ile Ser
365                 370                 375                 380 gga gta gcc ttt gtt gtc aca aga ttt act gac ctt ata agc tgt gtc      1323
```

```
                                                                                      -continued Gly Val Ala Phe Val Val Thr Arg Phe Thr Asp Leu Ile Ser Cys Val
                385                 390                 395
act gga ata aac cca tat gtg ata gca ttc aca gca ctc gca agt gga        1371
Thr Gly Ile Asn Pro Tyr Val Ile Ala Phe Thr Ala Leu Ala Ser Gly
                400                 405                 410
act tca tgg cca gac tta gta gca agt aaa atc gct gca gag cga caa        1419
Thr Ser Trp Pro Asp Leu Val Ala Ser Lys Ile Ala Ala Glu Arg Gln
                415                 420                 425
cta acc gca gat tca gct att gca aac atc acc tgc agt aac tcg gtg        1467
Leu Thr Ala Asp Ser Ala Ile Ala Asn Ile Thr Cys Ser Asn Ser Val
            430                 435                 440
aac atc tat gtg ggg att gga gtt ccg tgg ctg ata aac aca gtc tac        1515
Asn Ile Tyr Val Gly Ile Gly Val Pro Trp Leu Ile Asn Thr Val Tyr
445                 450                 455                 460
aac tac ttt gca tac aga gag cct tta tac ata gaa aac gct aaa gga        1563
Asn Tyr Phe Ala Tyr Arg Glu Pro Leu Tyr Ile Glu Asn Ala Lys Gly
                465                 470                 475
tta agc ttt tcg ctt ctg ata ttc ttt gcg aca tca gtg gga tgt atc        1611
Leu Ser Phe Ser Leu Leu Ile Phe Phe Ala Thr Ser Val Gly Cys Ile
                480                 485                 490
gtg gtg ctt gtg ttg aga agg ttg att ata gga gct gag ctt gga ggt        1659
Val Val Leu Val Leu Arg Arg Leu Ile Ile Gly Ala Glu Leu Gly Gly
            495                 500                 505
cca agg cta tgg gct tgg ctt act tct gcc tat ttc atg atg ctt tgg        1707
Pro Arg Leu Trp Ala Trp Leu Thr Ser Ala Tyr Phe Met Met Leu Trp
        510                 515                 520
gtc gtc ttc gtt gtt ctt tct tct ttg aaa gtt tca ggc gtc ata tag        1755
Val Val Phe Val Val Leu Ser Ser Leu Lys Val Ser Gly Val Ile
525                 530                 535 aagaagcaac aaaaggaaaa accccatgag tagaagaaaa agtcttagct tacttgcaca     1815
tgtctcagtt tttgttttc ttacttgtta aggggttttt atataattat caaagttcaa     1875
aggcagttgg ctaaatatgt gttgcaaata taaatcatat tgactatgat tttggaggct    1935

<210> SEQ ID NO 4
<211> LENGTH: 2803
<212> TYPE: DNA
<213> ORGANISM: Arabidopsis thaliana

<400> SEQUENCE: 4
ccggtacgtc cgcattgatc aatttcgtcg cgtggctcac tctgtttcat ctgttctttt      60
cttatttttt agctattttt gttgagattt gttcgttgaa aattatggtt ttgtgaaaag     120
aacccaactt gttttactga acccatgatg aaagttataa tcttttgatc tggttaccct     180
tggattttga ttacgcatac agtggaacat gcaattgtta ttagcattgg ttatagattg     240
gatttcggtt acatgccatt ggatccgttg caatgtttag tttgtgttac agattctctg     300
gaaagaaatc ttttttgcatg ttccgtttgt ttcgcatcct cttgatactg ttcgatcgat    360
caggctacag gtttcatcag tttcttctaa aagttgtaag cttcttttg gtgtgccaga     420 ttctttccc cagtgaggac aagtgttcag ttgacttatt aggaggtggg gtttgaataa     480
gttacaatgg cctcaattct taatcaaacc aggagttgc aagaatcttc taaggttctt     540
gggcatttaa gatgtgaaaa cttctttcta ttccccggag aaaacacttt gtcagatggt    600 ttgagggggtg tgttatattt tctcggtctt gcctactgct ttattgggtt gtcagccatc    660
actgcacggt tcttcaagtc tatggagaat gtcgtgaaac attcccgtaa agtggttaca    720
attgatccca ttactaaagc tgaagtcatc acatacaaga aagtttggaa ctttactatt    780
```

-continued

| | |
|---|---|
| gcagacatca gtttgttggc gtttggaact agcttccctc agatttcttt ggctaccatc | 840 |
| gatgcaatac ggaatatggg ggagcggtat gctggaggtc tggtggttgt tcctttcttc | 900 |
| cttccaaaac tctagttttt acttttaagt tcatgaattc ttatatcatg ttttgtcata | 960 |
| taggtcttgg tcctggaaca cttgttggct cagctgcatt tgatcttttc cccatccacg | 1020 |
| ctgtttgtgt cgttgtgcca aaagctggag aactgaaaaa gatatccgac ttaggtgttt | 1080 |
| ggctagttga gctcgtatgg tcttttttggg cttacatctg gctatacata atcctcgagg | 1140 |
| taactgtgaa aagcggttta aacagattct gttgagtcta tactctatac tgataaggtc | 1200 |
| taaaaatctg tttctttttca cgtctcacag gtgtggtcac caaacgtaat tacacttgtg | 1260 |
| gaggcattat tgacagtact gcaatacgga ttgcttctag ttcatgcgta cgcccaagac | 1320 |
| aagcgatggc cttacttgtc tttaccaatg tgggtttctt ttccagacaa taatattagt | 1380 |
| tccttcaaaa tggatttcta ctaaagattg tatctttgtg tttgtatttg atacttgcag | 1440 |
| gtcaagaggt gataggccag aggagtgggt tccagaggag attgatacat ccaaagatga | 1500 |
| caatgacaat gatgttcatg atgtgtattc ggatgctgct caagatgctg ttaatcgggg | 1560 |
| aagcagaaac attgttgata tcttctctat tcattcagct aacaatgata caggtactaa | 1620 |
| gtatgattag gctgtctatt ctattgatat aagatcagtt ttagcgtatt tgcttatttc | 1680 |
| caaatctatg tgattcccat atttatctct ggtagtatat tgttataaat caaactttcc | 1740 |
| ctgtaacaaa cacttttgca gggatcactt atcatactgt ggcagatact ccacccgatt | 1800 |
| ctgcgactaa gaagggtaag gcgaagaatt ctactgtttt tgacatttgg aaacatcaat | 1860 |
| tcgtggatgc aataacggta aaaatcttca acttaccaag tgttttctag attcttctat | 1920 |
| atcctatttt gggcttttga tcattatcaa cacatctttc ttaacttgtt tctcttccta | 1980 |
| ttcgtaatca aacagttgga aacatcagaa tcaaagaaag tggatagcat ttatcttcga | 2040 |
| atcgcgaaat ctttctggca tttactcctc gccccttgga aactgctttt tgcatttgtg | 2100 |
| ccccctgca acattgctca cggttggatc gctttcatct gctctctcct cttcatcagt | 2160 |
| ggagtagcct ttgttgtcac aagatttact gaccttataa gctgtgtcac tggtacacac | 2220 |
| cctcaccgct ttcaaaaact gaagttataa gattaaacat ttgagctcta aacattaga | 2280 |
| aactcttttc atcttgcagg aataaaccca tatgtgatag cattcacagc actcgcaagt | 2340 |
| ggaacttcat ggccagactt agtagcaagt aaaatcgctg cagagcgaca actaaccgca | 2400 |
| gattcagcta ttgcaaacat cacctgcagg taaaaatctc aaaaccctttt acaaacattg | 2460 |
| aagatctttt catgatcttt ttggtgataa attatgcagt aactcggtga acatctatgt | 2520 |
| ggggattgga gttccgtggc tgataaaacac agtctacaac tactttgcat acagagagcc | 2580 |
| tttatacata gaaaacgcta aaggattaag cttttcgctt ctgatattct ttgcgacatc | 2640 |
| agtgggatgt atcgtggtgc ttgtgttgag aaggttgatt ataggagctg agcttggagg | 2700 |
| tccaaggcta tgggcttggc ttacttctgc ctatttcatg atgctttggg tcgtcttcgt | 2760 |
| tgttctttct tctttgaaag tttcaggcgt catatagaag aag | 2803 |

<210> SEQ ID NO 5
<211> LENGTH: 474
<212> TYPE: PRT
<213> ORGANISM: Arabidopsis thaliana

<400> SEQUENCE: 5

Met Glu Asn Val Val Lys His Ser Arg Lys Val Val Thr Ile Asp Pro
1               5                   10                  15

-continued

```
Ile Thr Lys Ala Glu Val Ile Thr Tyr Lys Lys Val Trp Asn Phe Thr
             20                  25                  30

Ile Ala Asp Ile Ser Leu Leu Ala Phe Gly Thr Ser Phe Pro Gln Ile
             35                  40                  45

Ser Leu Ala Thr Ile Asp Ala Ile Arg Asn Met Gly Glu Arg Tyr Ala
     50                  55                  60

Gly Gly Leu Gly Pro Gly Thr Leu Val Gly Ser Ala Ala Phe Asp Leu
65                   70                  75                  80

Phe Pro Ile His Ala Val Cys Val Val Pro Lys Ala Gly Glu Leu
                 85                  90                  95

Lys Lys Ile Ser Asp Leu Gly Val Trp Leu Val Glu Leu Val Trp Ser
             100                 105                 110

Phe Trp Ala Tyr Ile Trp Leu Tyr Ile Ile Leu Glu Val Trp Ser Pro
             115                 120                 125

Asn Val Ile Thr Leu Val Glu Ala Leu Leu Thr Val Leu Gln Tyr Gly
             130                 135                 140

Leu Leu Leu Val His Ala Tyr Ala Gln Asp Lys Arg Trp Pro Tyr Leu
145                 150                 155                 160

Ser Leu Pro Met Ser Arg Gly Asp Arg Pro Glu Glu Trp Val Pro Glu
                 165                 170                 175

Glu Ile Asp Thr Ser Lys Asp Asn Asp Asn Asp Val His Asp Val
             180                 185                 190

Tyr Ser Asp Ala Ala Gln Asp Ala Val Glu Ser Gly Ser Arg Asn Ile
             195                 200                 205

Val Asp Ile Phe Ser Ile His Ser Ala Asn Asn Asp Thr Gly Ile Thr
    210                 215                 220

Tyr His Thr Val Ala Asp Thr Pro Pro Asp Ser Ala Thr Lys Lys Gly
225                 230                 235                 240

Lys Ala Lys Asn Ser Thr Val Phe Asp Ile Trp Lys His Gln Phe Val
                245                 250                 255

Asp Ala Ile Thr Val Lys Ile Phe Asn Leu Pro Lys Val Asp Ser Ile
             260                 265                 270

Tyr Leu Arg Ile Ala Lys Ser Phe Trp His Leu Leu Ala Pro Trp
    275                 280                 285

Lys Leu Leu Phe Ala Phe Val Pro Pro Cys Asn Ile Ala His Gly Trp
    290                 295                 300

Ile Ala Phe Ile Cys Ser Leu Leu Phe Ile Ser Gly Val Ala Phe Val
305                 310                 315                 320

Val Thr Arg Phe Thr Asp Leu Ile Ser Cys Val Thr Gly Ile Asn Pro
                325                 330                 335

Tyr Val Ile Ala Phe Thr Ala Leu Ala Ser Gly Thr Ser Trp Pro Asp
             340                 345                 350

Leu Val Ala Ser Lys Ile Ala Ala Glu Arg Gln Leu Thr Ala Asp Ser
             355                 360                 365

Ala Ile Ala Asn Ile Thr Cys Ser Asn Ser Val Asn Ile Tyr Val Gly
    370                 375                 380

Ile Gly Val Pro Trp Leu Ile Asn Thr Val Tyr Asn Tyr Phe Ala Tyr
385                 390                 395                 400

Arg Glu Pro Leu Tyr Ile Glu Asn Ala Lys Gly Leu Ser Phe Ser Leu
                405                 410                 415

Leu Ile Phe Phe Ala Thr Ser Val Gly Cys Ile Val Val Leu Val Leu
             420                 425                 430

Arg Arg Leu Ile Ile Gly Ala Glu Leu Gly Gly Pro Arg Leu Trp Ala
```

```
                435                 440                 445
Trp Leu Thr Ser Ala Tyr Phe Met Met Leu Trp Val Val Phe Val Val
    450                 455                 460

Leu Ser Ser Leu Lys Val Ser Gly Val Ile
465                 470

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide
<221> NAME/KEY: modified_base
<222> LOCATION: (12)..(12)
<223> OTHER INFORMATION: i
<221> NAME/KEY: modified_base
<222> LOCATION: (18)..(18)
<223> OTHER INFORMATION: i

<400> SEQUENCE: 6
caygaraarg tncarggngg                                              20

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide
<221> NAME/KEY: modified_base
<222> LOCATION: (9)..(9)
<223> OTHER INFORMATION: i
<221> NAME/KEY: modified_base
<222> LOCATION: (12)..(12)
<223> OTHER INFORMATION: i
<221> NAME/KEY: modified_base
<222> LOCATION: (15)..(15)
<223> OTHER INFORMATION: i

<400> SEQUENCE: 7
gcccartgna rngcngtrtg                                              20

<210> SEQ ID NO 8
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 8
gggggaacgc ttgaccgatt c                                            21

<210> SEQ ID NO 9
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 9
ccgggcctcc aaaatcatag t                                            21

<210> SEQ ID NO 10
<211> LENGTH: 21
<212> TYPE: DNA
<213> ORGANISM: Artificial Sequence
<220> FEATURE:
<223> OTHER INFORMATION: synthetic oligonucleotide
```

-continued

```
<400> SEQUENCE: 10
cccgtgatcg gcgtattgtg a                                              21

<210> SEQ ID NO 11
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 11
gccaactgcc tttgaacttt g                                              21

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 12
atgccgctca ccgagatatt                                                20

<210> SEQ ID NO 13
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 13
tcttctactc atggggtttt tc                                             22

<210> SEQ ID NO 14
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 14
ggggtttgaa taagttacca tggcctcaat tctta                               35

<210> SEQ ID NO 15
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 15
tcttctatat gacgcctgaa act                                            23

<210> SEQ ID NO 16
<211> LENGTH: 17
<212> TYPE: PRT
<213> ORGANISM: Artificial Sequence
<220> FEATURE:
<223> OTHER INFORMATION: synthetic peptide

<400> SEQUENCE: 16

Cys Glu Glu Ile Asp Thr Ser Lys Asp Asp Asn Asp Asn Asp Val His
1               5                   10                  15

Asp
```

-continued

```
<210> SEQ ID NO 17
<211> LENGTH: 16
<212> TYPE: PRT
<213> ORGANISM: Artificial Sequence
<220> FEATURE:
<223> OTHER INFORMATION: synthetic peptide

<400> SEQUENCE: 17

Cys Met Ser Arg Gly Asp Arg Pro Glu Glu Trp Val Pro Glu Glu Ile
1               5                   10                  15
```